(12) United States Patent  
Chou

(10) Patent No.: US 7,666,666 B2  
(45) Date of Patent: Feb. 23, 2010

(54) FUEL PRODUCTION

(75) Inventor: Chih-Chung Chou, Taoyuan County (TW)

(73) Assignee: Sunho Biodiesel Corporation, Taipei (TW)

( * ) Notice: Subject to any disclaimer, the term of this patent is extended or adjusted under 35 U.S.C. 154(b) by 814 days.

(21) Appl. No.: 11/232,467

(22) Filed: Sep. 20, 2005

(65) Prior Publication Data

US 2006/0063242 A1  Mar. 23, 2006

Related U.S. Application Data

(63) Continuation-in-part of application No. 10/945,339, filed on Sep. 20, 2004, now Pat. No. 7,473,539.

(51) Int. Cl.
*C12M 1/00* (2006.01)
*C12M 1/40* (2006.01)

(52) U.S. Cl. ............... 435/289.1; 435/294.1; 435/299.1

(58) Field of Classification Search ............... 435/299.1, 435/292.1, 289.1, 294.1
See application file for complete search history.

(56) References Cited

U.S. PATENT DOCUMENTS

| | | | |
|---|---|---|---|
| 4,855,233 | A | 8/1989 | Gancet et al. |
| 5,713,965 | A | 2/1998 | Foglia et al. |
| 6,398,707 | B1 | 6/2002 | Wu et al. |
| 2003/0004363 | A1 | 1/2003 | Koncar et al. |

FOREIGN PATENT DOCUMENTS

| | | |
|---|---|---|
| CA | 2368179 | 9/2000 |
| DE | 101 22 551 A1 | 11/2002 |
| EP | 0 413 307 A1 | 2/1991 |
| EP | 1 111 064 A1 | 6/2001 |
| FR | 2 617 501 | 1/1989 |
| JP | 6078587 | 5/1985 |
| JP | 62104589 | 5/1987 |
| JP | 63116697 | 5/1988 |
| JP | 05328962 A * | 12/1993 |
| WO | WO 0073254 A1 * | 12/2000 |

OTHER PUBLICATIONS

Abigor et al., "Lipase-catalyzed production of biodiesel fuel from some Nigerian lauric oil," Biochemical Society, 2000, 28:979-981.

(Continued)

*Primary Examiner*—William H Beisner
(74) *Attorney, Agent, or Firm*—Occhiuti Rohlicek & Tsao LLP

(57) ABSTRACT

An apparatus that includes a first reactor and a return mechanism. The first reactor has an inlet to receive a mixture comprising a first reactant, a second reactant, a reaction product, and an inert solvent that dissolves at least a portion of the first and second reactants, an enzyme to facilitate a reaction between the first and second reactants to generate more reaction product, and an outlet to output the reaction product, including the reaction product received at the inlet and the reaction product generated from the reaction between the first and second reactants. The return mechanism sends at least a portion of the reaction product from the outlet back to the inlet.

18 Claims, 20 Drawing Sheets

OTHER PUBLICATIONS

Deng et al., "Enzymatic production of fatty acid alkyl esters with a lipase preparation from *Candida* sp. 99-125," Eur. J. Lipid Sci. Technol., 2003, 105:727-734.

Soumanou et al., "Lipase-catalyzed alcoholysis of vegetable oils," Eur. J. Lipid Sci. Technol., 2003, 105:656-660.

Dossat et al., "Continuous enzymatic Transesterification of High Oleic Sunflower Oil in a Packed Bed Reactor: Influence of the Glycerol Production", Enzyme and Microbial Technology 24;194-200, 1999.

Fukuda et al., "Biodiesel Fuel Production by Transesterification of Oils", Journal of Bioscience and Bioengineering, 92:405-416, 2001.

Mittelbach, "Lipase Catalyzed Alcoholysis of Sunflower Oil", Journal of American Oil Chemists' Society, 168-170, 1989.

Shimada et al., "Enzymatic Alcoholysis for Biodiesel Fuel Production and Application of the Reaction to Oil Processing", Journal of Molecular Catalysis B: Enzymatic 17:133-142, 2002.

Soumanou et al., "Improvement in Lipase-Catalyzed Synthesis of Fatty Acid Methyl Esters from Sunflower Oil", Enzyme and Microbial Technology, 33:97-103, 2003.

Viklund, "Surfactants based on Natural Products— Enzymatic Synthesis and Functional Characterization", Kungl Tekniska Hogskolan, Department of Biotechnology, Royal Institute of Technology, 11-17, 2003.

Chen, Doctoral Thesis, "Process Development for Transesterification of Triglyceride and Its Application," 77-85, 2003.

\* cited by examiner

FUEL PRODUCTION

CROSS-REFERENCE TO RELATED APPLICATIONS

This application is a continuation-in-part of U.S. application Ser. No. 10/945,339, filed Sep. 20, 2004, now U.S. Pat. No. 7,473,539 titled "Methods for Producing Alkyl Esters," to Chih-Chung Chou, the contents of which are incorporated by reference.

BACKGROUND

This invention relates to fuel production, including bio-diesel fuel production from vegetable oils and animal fats.

An oil source of alcoholysis of vegetable oils and animal fats can be used to produce fatty acid alkyl esters, which can be used as diesel fuels, generally referred to herein as "bio-diesel" fuels. In one production approach, non-enzymatic catalysts, such as alkali hydroxides and alcoholates, are used to facilitate the alcoholysis. A by-product of the alcoholysis is glycerol. The non-enzymatic catalysts are removed with the glycerol, and cannot be reused. Purification of glycerol is made difficult because it contains a large amount of the catalyst. In another production approach, enzymatic catalysts, such as lipases, are used to facilitate production of alkyl esters from natural oils in an alcoholysis reaction. An oil source having triglyceride and an alcohol are dissolved in an organic solvent. With a lipase as a catalyst, the triglyceride and the alcohol react to produce alkyl ester, with glycerol as by-product.

SUMMARY

In a general aspect, an enzymatic transesterification approach for bio-diesel fuel production provides a high purity fuel, such as alkyl ester (and in some examples, by-product glycerol), in a cost efficient manner with less waste and reduced side product. The processing plant for the enzymatic transesterification can be made using a simple configuration that requires reduced capital investment.

In general, in one aspect, the invention features an apparatus that includes a first reactor having an inlet to receive a mixture comprising a first reactant, a second reactant, a reaction product, and an inert solvent that dissolves at least a portion of the first and second reactants, an enzyme to facilitate a reaction between the first and second reactants to generate more reaction product, and an outlet to output the reaction product, including the reaction product received at the inlet and the reaction product generated from the reaction between the first and second reactants. The apparatus includes a return mechanism to send at least a portion of the reaction product from the outlet back to the inlet.

Implementations of the invention may include one or more of the following features.

The reaction product includes alkyl ester. The return mechanism sends at least a portion of the alkyl ester back to the inlet. The mixture includes a solvent that dissolves at least a portion of the first reactant, the second reactant, and the reaction product. The outlet outputs at least the alkyl ester, the solvent, and unreacted first reactant.

The apparatus also includes an evaporator to evaporate the solvent to generate a mixture that includes the alkyl ester and the unreacted first reactant. The outlet also outputs glycerol. The apparatus also includes an evaporator to evaporate the solvent to generate a mixture that includes the alkyl ester, the glycerol, and the unreacted first reactant. The apparatus also includes a phase separator to separate the alkyl ester from the glycerol based on liquid-liquid phase separation.

The first reactant includes triglyceride. The first reactant includes a carboxylic acid. The second reactant includes at least one of a primary and secondary alcohol. The first reactant includes at least one of vegetable oil and animal fat. The reaction product has a composition that is suitable for use as fuel. The reaction product has a composition that is suitable for use as fuel for a diesel engine. The reaction product has a composition that is suitable for use as fuel for at least one of an internal combustion diesel engine and a gas turbine diesel engine.

The apparatus also includes a mixer having a first inlet to receive the first reactant, a second inlet to receive the second reactant, a third inlet to receive a portion of the reaction product from the outlet of the reactor, a fourth inlet to receive the inert solvent, and an outlet to output the mixture that includes the first reactant, the second reactant, the inert solvent, and the reaction product. The outlet also outputs other components, and the return mechanism also sends at least a portion of the other components back to the inlet. The enzyme facilitates a reaction between the other components and the second reactant to generate more reaction product. The other components include at least one of monoglyceride, diglyceride, triglyceride, and carboxylic acid.

The apparatus also includes a second reactor having an inlet to receive a mixture that includes additional second reactant and reaction product from the outlet of the first reactor, an enzyme to facilitate a reaction between the second reactant and the other components to generate more reaction product, and an outlet to output the reaction product, including the reaction product received at the inlet of the second reactor and the reaction product generated from the reaction between the second reactant and the other components.

The apparatus also includes an evaporator to evaporate the inert solvent and at least one of unreacted first reactant and unreacted second reactant. The apparatus also includes a short-path evaporator to separate the reaction product from remaining unreacted reactant. The reaction product includes alkyl ester. The reaction product includes at least 99% alkyl ester. The apparatus also includes a return mechanism to send at least a portion of the alkyl ester from the outlet of the second reactor back to the inlet of the first reactor. The first reactant includes triglyceride or carboxylic acid, and the second reactant includes primary or secondary alcohol.

In general, in another aspect, the invention features an apparatus that includes a reactor having an inlet to receive a mixture that includes reactants, an enzyme to facilitate a reaction between the reactants, and a feedback mechanism to send at least a portion of a product of the reaction back to the inlet.

Implementations of the invention may include one or more of the following features.

The product of the reaction includes alkyl ester, and the feedback mechanism sends at least a portion of the alkyl ester back to the inlet. The reactants include (1) at least one of triglyceride and carboxylic acid, and (2) at least one of primary and secondary alcohol. The enzyme includes a lipase.

In general, in another aspect, the invention features a system for generating alkyl ester that includes a first subsystem and a second subsystem. The first subsystem includes a first reactor having a first inlet to receive a first mixture that includes a first reactant, a second reactant, and an inert solvent to dissolve the first and second reactants, a first enzyme to facilitate a reaction between the first and second reactants to generate a reaction product, and a first outlet to output the reaction product, the inert solvent, and other components.

The second subsystem includes a second reactor having a second inlet to receive a second mixture that includes additional second reactant, an inert solvent, at least a portion of the reaction product, and the other components from the first outlet, a second enzyme to facilitate a reaction between the second reactant and the other components to generate more reaction product, and a second outlet to output the reaction product, including the reaction product received at the inlet of the second inlet and the reaction product generated from the reaction between second reactant and the other components.

Implementations of the invention may include one or more of the following features.

The reaction product includes alkyl ester. The system also includes a return mechanism to send at least a portion of the alkyl ester from the first outlet back to the first inlet. The system also includes a return mechanism to send at least a portion of the alkyl ester from the second outlet back to the first inlet. The percentage of alkyl ester in the reaction product at the output of the second reactor is higher than the percentage of alkyl ester in the reaction product at the output of the first reactor.

The second subsystem includes a separator to remove at least a portion of components other than alkyl ester from a first solution output from the second outlet to obtain a second solution that has at least 90% by weight of alkyl ester. The separator includes an evaporator. The separator includes a liquid-liquid separator.

The first subsystem includes a separator to remove at least a portion of components other than alkyl ester from a first solution output from the first outlet to obtain a second solution that has a higher concentration of alkyl ester than the first solution. The separator includes an evaporator. The separator includes a liquid-liquid separator.

In some examples, the first reactant includes triglyceride. In other examples, the first reactant includes carboxylic acid. The second reactant includes at least one of primary and secondary alcohol. The first subsystem includes a mixer having a first inlet to receive the first reactant, a second inlet to receive the second reactant, a third inlet to receive the inert solvent, a structure to mix the first reactant, the second reactant, and the inert solvent, and an outlet to output the first mixture that includes the first reactant, the second reactant, and the inert solvent. In some examples, the first enzyme is the same as the second enzyme. In other examples, the first enzyme is different from the second enzyme. At least one of the first and second enzymes includes a lipase.

In general, in another aspect, the invention features an apparatus that includes a reactor, a separation unit, and a return mechanism. The reactor has a pipeline to transmit a mixture that includes a first reactant, a second reactant, an inert solvent, and a reaction product that are in an homogeneous state, a coupler to receive a cartridge having an inlet to receive the mixture from the pipeline, an enzyme to facilitate a reaction between the first and second reactants to generate more reaction product, and an outlet to output the reaction product, including the reaction product received at the inlet and the reaction product generated from the reaction between the first and second reactants. The separation unit processes the output of the outlet to produce a solution having a higher percentage of the reaction product. The return mechanism sends at least a portion of the solution back to the pipeline.

In general, in another aspect, the invention features a system for generating alkyl ester that includes a first subsystem and a second subsystem. The first subsystem includes a first reactor having a first pipeline to transmit a first mixture that includes a first reactant, a second reactant, an inert solvent, and alkyl ester that are in a homogeneous state, a first coupler to receive a first cartridge having a first inlet to receive the mixture from the first pipeline, a first enzyme to facilitate a reaction between the first and second reactants to generate alkyl ester, and a first outlet to output the alkyl ester, the solvent, and other components. The second subsystem includes a second reactor having a second pipeline transmit a second mixture that includes additional second reactant, inert solvent, and at least a portion of the alkyl ester and the other components from the first outlet, a second coupler to receive a second cartridge having a second inlet to receive the mixture from the second pipeline, a second enzyme to facilitate a reaction between the second reactant and the other components to generate more alkyl ester, and a second outlet to output the alkyl ester.

In general, in another aspect, the invention features a system for generating alkyl ester that includes a cartridge to receive a mixture that includes a first reactant and a second reactant, the cartridge including an enzyme to facilitate a reaction between the first and second reactants to generate a reaction product, the cartridge having an identifier; and a controller to control an operation condition of the system based on the identifier on the cartridge.

Implementations of the invention may include one or more of the following features.

The reaction product includes alkyl ester. The enzyme includes a lipase. The controller controls a speed of a pump based on the identifier, in which the speed of the pump affects the speed in which the solution passes through the cartridge. The controller controls a heater based on the identifier, in which the heater affects a temperature of the solution. The controller determines when to send a signal indicating that the cartridge needs to be replaced based on the identifier.

In general, in another aspect, the invention features an apparatus that includes a first reactor having an inlet to receive an oil source and a reactant, and an enzyme to facilitate a reaction between the oil source and the reactant to generate a desired product and other components; and a first separator to separate the desired product from the other components to generate a desired crude product; and a return mechanism to send at least a portion of the crude desired product back to the inlet of the first reactor.

Implementations of the invention may include one or more of the following features.

The desired product includes a fuel. The desired product includes alkyl ester.

The apparatus also includes a second reactor having an inlet to receive a mixture that includes additional reactant and at least a portion of the crude desired product, and an enzyme to facilitate a reaction between the reactant and components in the crude desired product to generate additional desired product; and a second separator to separate the desired product from other components to generate a high purity desired product.

The oil source includes at least one of triglyceride and carboxylic acid. The crude fuel includes alkyl ester. The reactant includes at least one of primary and secondary alcohol. The enzyme includes lipase.

In general, in another aspect, the invention features an apparatus that includes a cartridge including an enzyme, the cartridge configured to be coupled to an alkyl ester generator. The alkyl ester generator includes a mixer that mixes a first reactant, a second reactant, an inert solvent, and alkyl ester to generate a solution that is passed through the cartridge, in which the enzyme in the cartridge facilitates a reaction between the first and second reactants to generate more alkyl ester, and a return mechanism to send at least a portion of the alkyl ester derived from the reaction between the first and second reactants back to the mixer.

Implementations of the invention may include one or more of the following features.

The enzyme includes a lipase. The cartridge includes information on the cartridge related to an operation of the alkyl ester generator.

In general, in another aspect, the invention features an apparatus that includes a cartridge including an enzyme, the cartridge configured to be coupled to a first subsystem of a two-stage system that generates alkyl ester. The first subsystem receives a first reactant, a second reactant, and an inert solvent, and passes a mixture that includes the first reaction, the second reactant, and the inert solvent through the cartridge, the enzyme facilitating a reaction between the first and second reactants to generate a first product, in which the first product is processed by a first separator to generate a crude product having a first percentage of alkyl ester. The second subsystem receives the crude product and additional second reactant, and generates a second product, in which the second product is processed by a second separator to generate a refined product having a second percentage of alkyl ester that is higher than the first percentage.

In general, in another aspect, the invention features an apparatus that includes a cartridge including an enzyme, the cartridge configured to be coupled to a second subsystem of a two-stage system that generates alkyl ester. The first subsystem receives a first reactant and a second reactant, and generates a crude product having a first percentage of alkyl ester. The second subsystem receives the crude product and additional second reactant, passes a mixture that includes the crude product and the additional second reactant through the cartridge, the enzyme facilitating a reaction between components in the crude product and the second reactant to generate an output, in which the output is processed by a separation unit to generate a refined product having a second percentage of alkyl ester that is higher than the first percentage.

In general, in another aspect, the invention features an apparatus that includes a cartridge including a lipase, the cartridge configured to be coupled to an alkyl ester generator. The alkyl ester generator includes a mixer to mix an oil source and a primary alcohol or a secondary alcohol in an organic solvent to form a solution that is passed through the cartridge, in which the oil source includes a triglyceride and the lipase facilitates a reaction between the triglyceride and the primary alcohol or the secondary alcohol to generate an alkyl ester, in which the solution does not undergo phase separation throughout the reaction and glycerol is produced as a by-product. The alkyl ester generator also includes an evaporator to remove the organic solvent and unreacted primary alcohol or secondary alcohol, a phase separator to separate the alkyl ester from the glycerol, and a second separator to separate the alkyl ester from unreacted oil source.

Implementations of the invention may include one or more of the following features. The second separator includes a short-path evaporator.

In general, in another aspect, the invention features an apparatus that includes a cartridge including a lipase, the cartridge configured to be coupled to an alkyl ester generator. The alkyl ester generator includes a mixer to mix an oil source and a primary alcohol or a secondary alcohol in an organic solvent to form a solution that is passed through the cartridge, in which the oil source includes a carboxylic acid and the lipase facilitates a reaction between the carboxylic acid and the primary alcohol or the secondary alcohol to generate an alkyl ester, in which the solution does not undergo phase separation throughout the reaction and water is produced as a by-product. The alkyl ester generator also includes an evaporator to remove the organic solvent and unreacted primary alcohol or secondary alcohol, and a separator to separate the alkyl ester from unreacted oil source.

Implementations of the invention may include one or more of the following features. The separator includes a short-path evaporator.

In general, in another aspect, the invention features an apparatus that includes an evaporator having an input to receive a mixture that includes alkyl ester, alcohol, a inert solvent, and glycerol, the evaporator to evaporate the inert solvent and the alcohol to generate a solution including alkyl ester and glycerol, and a separator having an input to receive the solution, the separator to separate the alkyl ester from the glycerol based on liquid-liquid phase separation.

In general, in another aspect, the invention features a power generator that includes an enzyme-based alkyl ester generator and an electricity generator. The alkyl ester generator includes an inlet to receive a mixture that includes reactants, an enzyme to facilitate a reaction between the reactants to generate alkyl ester, and a feedback mechanism to send at least a portion of the alkyl ester from the outlet back to the inlet. The electricity generator that includes an inlet to receive the alkyl ester generated by the alkyl ester generator, a converter to convert energy in the alkyl ester into electricity, and an outlet to output the electricity generated by the converter.

Implementations of the invention may include one or more of the following features.

At least a portion of the alkyl ester generator is powered by the electricity generated by the electricity generator. The reactants include triglyceride and alcohol.

In general, in another aspect, the invention features a vehicle that includes a storage to store reactants; an enzyme-based alkyl ester generator, and an engine. The alkyl ester generator includes an inlet to receive a mixture that includes the reactants, an enzyme to facilitate a reaction between the reactants to generate alkyl ester, and a feedback mechanism to send at least a portion of the alkyl ester from the outlet back to the inlet. The engine includes an inlet to receive the alkyl ester generated by the alkyl ester generator, and a converter to convert energy in the alkyl ester into kinetic energy.

Implementations of the invention may include one or more of the following features.

At least a portion of the alkyl ester generator is powered by the kinetic energy generated by the engine. In some examples, the vehicle also includes transmission mechanism to transmit the kinetic energy to wheels. In some examples, the vehicle also includes transmission mechanism to transmit the kinetic energy to propellers.

In general, in another aspect, the invention features a vehicle that includes a storage to store reactants, an enzyme-based alkyl ester generator, and an electricity generator. The alkyl ester generator includes an inlet to receive a mixture that includes the reactants, an enzyme to facilitate a reaction between the reactants to generate alkyl ester, and a feedback mechanism to send at least a portion of the alkyl ester from the outlet back to the inlet. The electricity generator includes an input to receive the alkyl ester generated by the alkyl ester generator, a converter to convert energy in the alkyl ester into electricity, and an output to output the electricity generated by the converter. The vehicle also includes electronic components, and power lines to transmit at least a portion the electricity generated by the electricity generator to the electronic components.

Implementations of the invention may include one or more of the following features. In some examples, the vehicle includes an air plane. In some examples, the vehicle includes a car. In some examples, the vehicle includes a ship.

In general, in another aspect, the invention features a building that includes a kitchen to process food; a storage to store recycled oil used in processing the food; and an enzyme-based alkyl ester generator. The alkyl ester generator includes an inlet to receive a mixture that includes the recycled oil and a reactant, an enzyme to facilitate a reaction between the recycled oil and the reactant to generate alkyl ester, and a feedback mechanism to send at least a portion of the alkyl ester from the outlet back to the inlet.

Implementations of the invention may include one or more of the following features.

The building also includes an electricity generator that includes an input to receive the alkyl ester generated by the alkyl ester generator, a converter to convert energy in the alkyl ester into electricity, and an output to output the electricity generated by the converter; and power lines to transmit at least a portion of the electricity to the building.

In general, in another aspect, the invention features an apparatus for producing an alkyl ester, the apparatus including a mixer to mix an oil source and a primary alcohol or a secondary alcohol in an organic solvent to form a solution, the oil source including a triglyceride; a reactor to receive the solution, the reactor including a lipase that facilitates a reaction between the triglyceride and the primary alcohol or the secondary alcohol to generate an alkyl ester, in which glycerol is produced as a by-product; an evaporator to remove the organic solvent and unreacted primary alcohol or secondary alcohol; and a phase separator to separate the alkyl ester from the glycerol.

Implementations of the invention may include one or more of the following features.

The solution received by the reactor does not undergo phase separation throughout the reaction. Each molecule of the organic solvent includes a number of carbon atoms and a heteroatom, in which the number ranges from 4 to 8. The organic solvent includes a C4 to C8 tertiary alcohol. The organic solvent includes at least one of t-butanol, 2-methyl-2-butanol, 2,3-dimethyl-2-butanol, 2-methyl-2-pentanol, 3-methyl-3-pentanol, 3-ethyl-3-pentanol, 2,3-dimethyl-2-pentanol, 2,3-dimethyl-3-pentanol, 2,2,3-trimethyl-3-pentanol, 2-methyl-2-hexanol, and 3-methyl-3-hexanol. The organic solvent includes pyridine. At least one of the primary alcohol and the secondary alcohol consists of 1 to 18 carbon atoms. The oil source includes at least one of plant oil, animal oil, and waste grease.

The apparatus also includes a carrier, in which the lipase is immobilized on the carrier. The lipase includes at least one of *candida antarctica* lipase, *thermomyces lanuginosa* lipase, *pseudomonas fluorescens* lipase, *pseudomonas cepacia* lipase, and *chromobacterium viscosum* lipase. A portion of the reactor is maintained at a reaction temperature of 0 to 95° C. to facilitate the reaction between the triglyceride and the primary alcohol or the secondary alcohol. The apparatus also includes a pump configured to cause the solution to flow through the reactor in 1 to 180 minutes.

The apparatus also includes a heater to heat the oil source to a range of 150 to 215° C. The heated oil source is cooled to the reaction temperature before the oil source is sent to the mixer. The apparatus also includes an inlet to add an alkyl ester to the solution before the solution is sent to the reactor. The apparatus also includes a return mechanism to allow at least a portion of the alkyl ester separated by the phase separator to enter the inlet and add to the solution.

In general, in another aspect, the invention features a method that includes inserting a cartridge into an alkyl ester generator, the cartridge having an inlet, and outlet, and an enzyme positioned between the inlet and the outlet; reading information encoded on the cartridge; controlling an operation of the alkyl ester generator based on the information.

Implementations of the invention may include one or more of the following features. Controlling an operation of the alkyl ester generator includes controlling at least one of temperature and flow rate of a solution flowing into the inlet of the cartridge.

In general, in another aspect, the invention features a method of processing food, the method including processing food using oil; recycling the oil used to process the food; receiving a mixture that includes recycled oil, a reactant, and an inert solvent; using enzyme to facilitate a reaction between the recycled oil and the reactant to generate alkyl ester; recycling at least a portion of the alkyl ester by mixing at least a portion of the alkyl ester with the mixture, the alkyl ester assisting in dissolving the recycled oil and the reactant; generating electricity or kinetic energy from the alkyl ester; and powering devices used for processing the food using the electricity or the kinetic energy.

In general, in another aspect, the invention features a method of operating a vehicle, the method including receiving a mixture that includes reactants and an inert solvent, passing the mixture through a cartridge of enzyme to facilitate a reaction between the reactants to generate alkyl ester; recycling at least a portion of the alkyl ester by mixing at least a portion of the alkyl ester with the mixture, the alkyl ester assisting in dissolving the reactants; generating electricity or kinetic energy from the alkyl ester; and powering devices used for operating the vehicle using the electricity or the kinetic energy.

Other features and advantages of the invention are apparent from the following description, and from the claims.

All of the publications, patent applications, patents, or other references mentioned are incorporated by reference. In case of conflict with the references incorporated by reference, the present specification, including definitions, will control.

DESCRIPTION OF DRAWINGS

FIG. 2A is a single stage plant with feedback of crude bio-diesel. FIG. 2B is a two-stage plant with feedback of crude bio-diesel from the first stage. FIG. 2C is a one-stage plant. FIG. 2D is a two-stage plant.

DESCRIPTION

1 Overview

Figure 1:
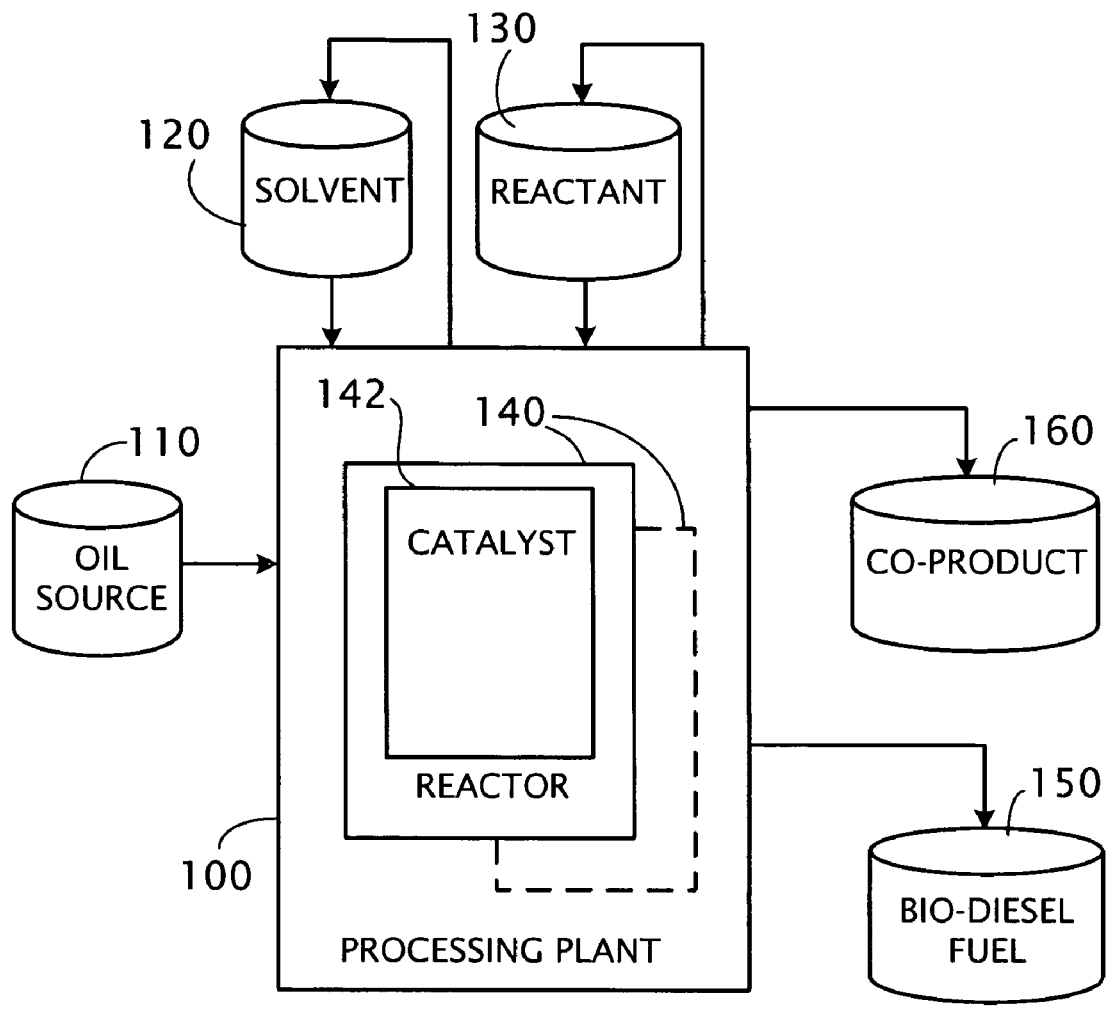
FIG. 1 is a block diagram of a fuel production system.

Referring to FIG. 1, a fuel production system includes a processing plant 100 that takes an oil source 110, such as soybean oil, and produces a bio-diesel fuel 150, such as alkyl ester, or a related product such as lubricating oil or a chemical intermediate. The processing plant 100 uses one or more reactors 140 that each makes use of an enzymatic catalyst 142. The processing plant makes use of an inert solvent 120, such as an anhydrous tertiary alcohol or anhydrous pyridine, as well as a reactant 130, such as a primary or secondary alcohol such as anhydrous methanol. During processing, the processing plant 100 recovers some of the inert solvent 120 and reactant 130 to replenish the supply. The processing plant also produces coproducts 160, such as waste water or glycerol.

A number of different versions of the processing plant are described below. These versions differ, for example, in features such as the number of reactor processing stages (for example, single stage with one reactor, two stage with two reactors), feedback arrangement of intermediate crude bio-diesel to prior stage reactors, and in the particular oil source, inert solvent, reactant, bio-catalyst and associated operating conditions used. For example, the processing plant can operate in a continuous flow mode, or alternatively in a batch mode.

Different versions of the processing plant may have different physical sizes. In one example, the plant is relatively compact, for example, the size of a refrigerator, permitting deployment at the point where the bio-diesel fuel is consumed, such as at the location of a diesel motor used for electricity generation. Other versions may be significantly larger with correspondingly greater production capacity. In some examples, the plant can be designed for home use, have sizes that are similar to a large refrigerator, and can have a production capacity of 200 liters per day or less. In other examples, the plant can be designed for farm, mall, or military field use, and have a size similar to containers having a length in a range of 20 to 40 feet. In other examples, the plant 100 can be designed for a commercial plant and have a capacity ranging from 40,000 tons to more than 250,000 tons annually.

1.1 Plant Configurations

Figure 2A:
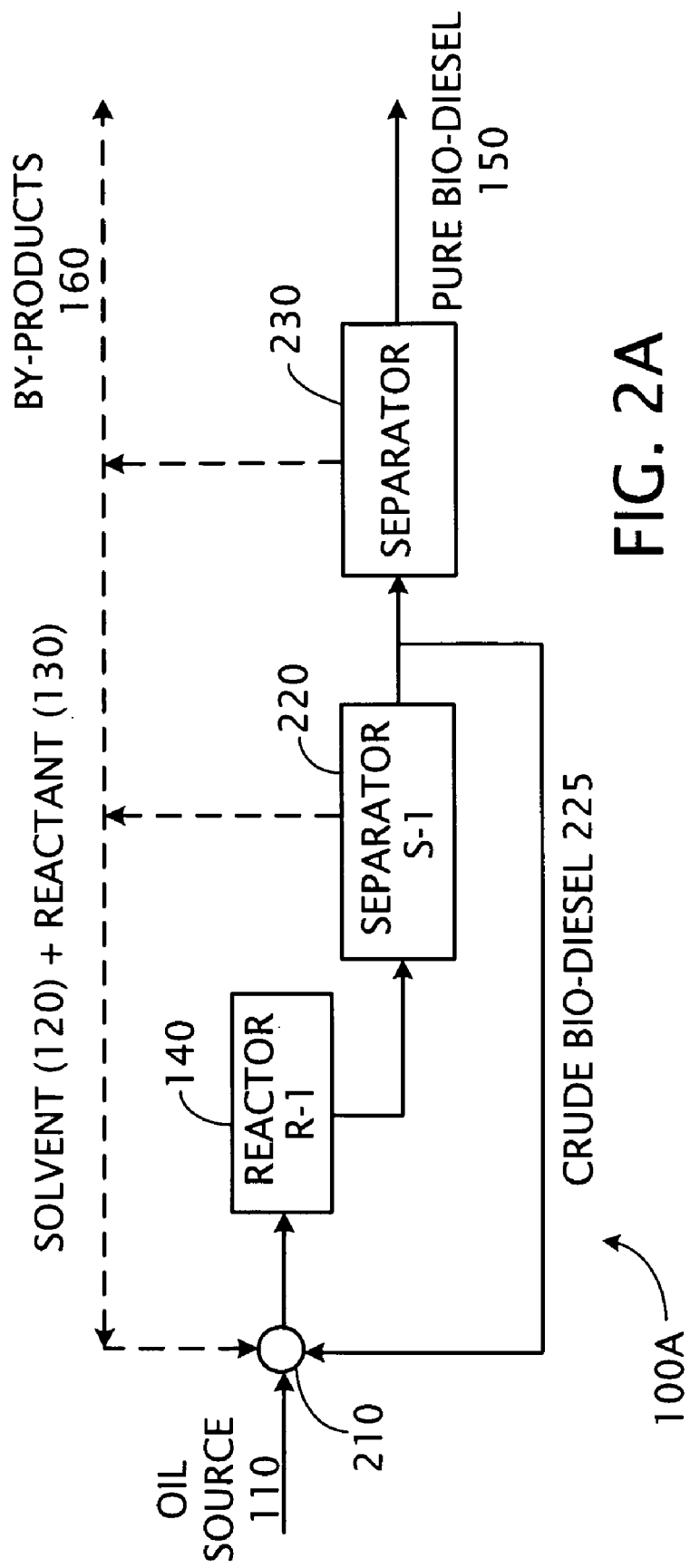
FIGS. 2A-2D are block diagrams of different configurations of a fuel production plant.

Referring to FIGS. 2A-D, four exemplary plant configurations make use of different numbers of stages and different types of feedback. Referring to FIG. 2A, a single-stage plant makes use of a single reactor 140. The output of the reactor (R-1) 140 is fed to a separator (S-1) 220, which includes components to separate inert solvent 120, unreacted reactant 130, and byproducts 160 from the reactor output to produce a crude bio-diesel product 225, for example, using a combination of an evaporator and a liquid-liquid separator. The input of reactor R-1 140 is provided from the output of a mixer 210, which accepts the oil source 110, inert solvent 120 and reactant 130. In this version of the plant, the mixer 210 also receives some of the crude bio-diesel 225 available from the output of the separator S-1. This feedback of the crude bio-diesel has two advantages: (1) enhance the completeness of the reaction among the reactants, and (2) reduce the amount of inert solvent required to be combined in the mixer 210. The output of the separator 220 is fed to a final separator 230, for example, a short path evaporator or a short-path distillation, which further purifies the bio-diesel to produce the output "pure" bio-diesel 150. As an example, the crude bio-diesel 225 may be 90-99% pure by weight, and the pure bio-diesel 150 may be greater than 99% pure by weight. This version of the plant has relatively few components that therefore is suitable for small and portable versions, as well as larger versions.

Figure 2B:
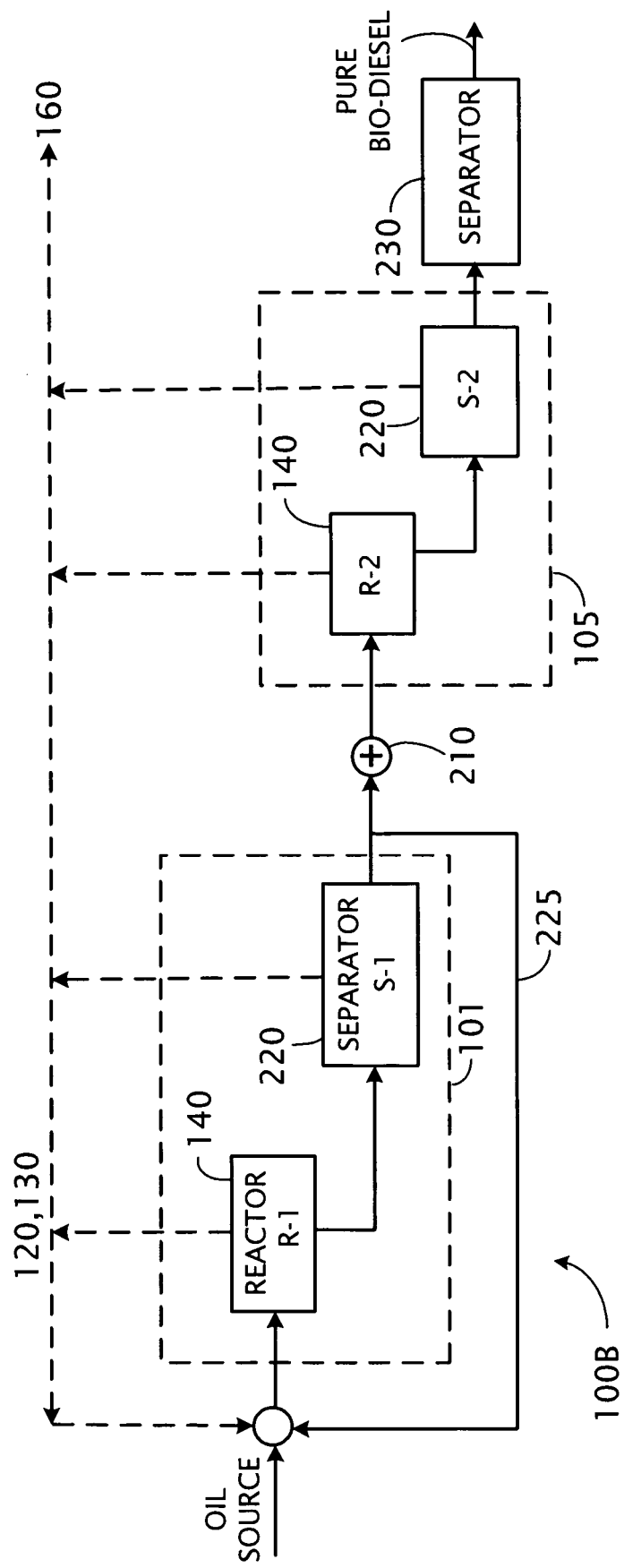

Referring to FIG. 2B, a two-stage plant 100B makes use of two stages 101 and 105, each including a reactor 140. The arrangement of a first reactor (R-1) 140 and a first separator (S-1) 220 are similar to that shown in FIG. 2A, including using a feedback of crude bio-diesel 225 from the output of the first separator 220 to the mixer 210 for the first reactor 140. In this version of the plant, the output of the first separator 220 is fed to a second mixer 210 that combines the crude bio-diesel 225 with further inert solvent 120 and reactant 130. The output of the second mixer 210 is fed to a second reactor (R-2) 140. The output of the second reactor 140 is passed through a second separator (S-2) 220. The output of the second separator 220 can be used directly as the bio-diesel fuel 150, or preferably passed through a final separator 230 prior to output. As an example, in such a two-stage plant, the crude bio-diesel 225 output from the first separator 220 is at least 90% pure by weight, while the output of the second separator is at least 95% pure.

Figure 2C:
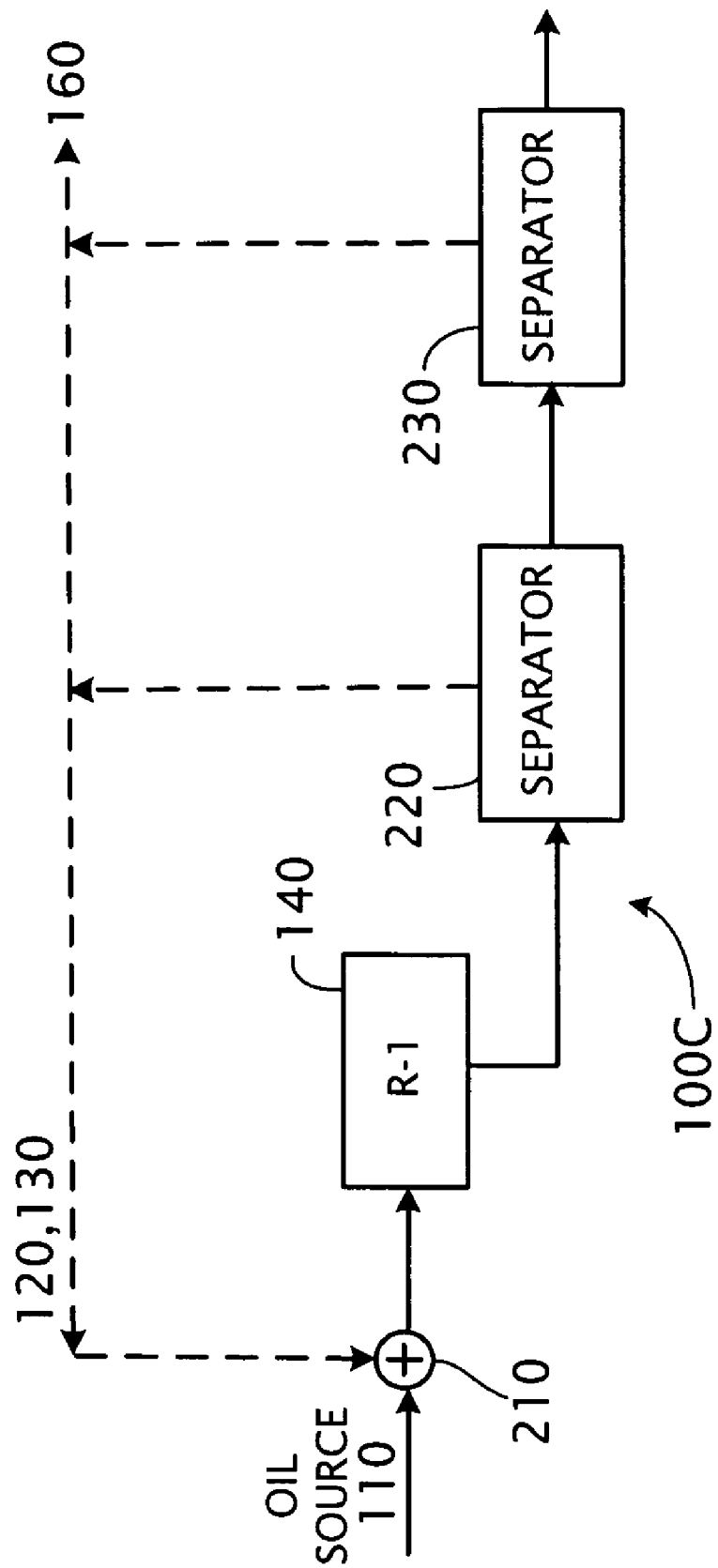
Figure 2D:
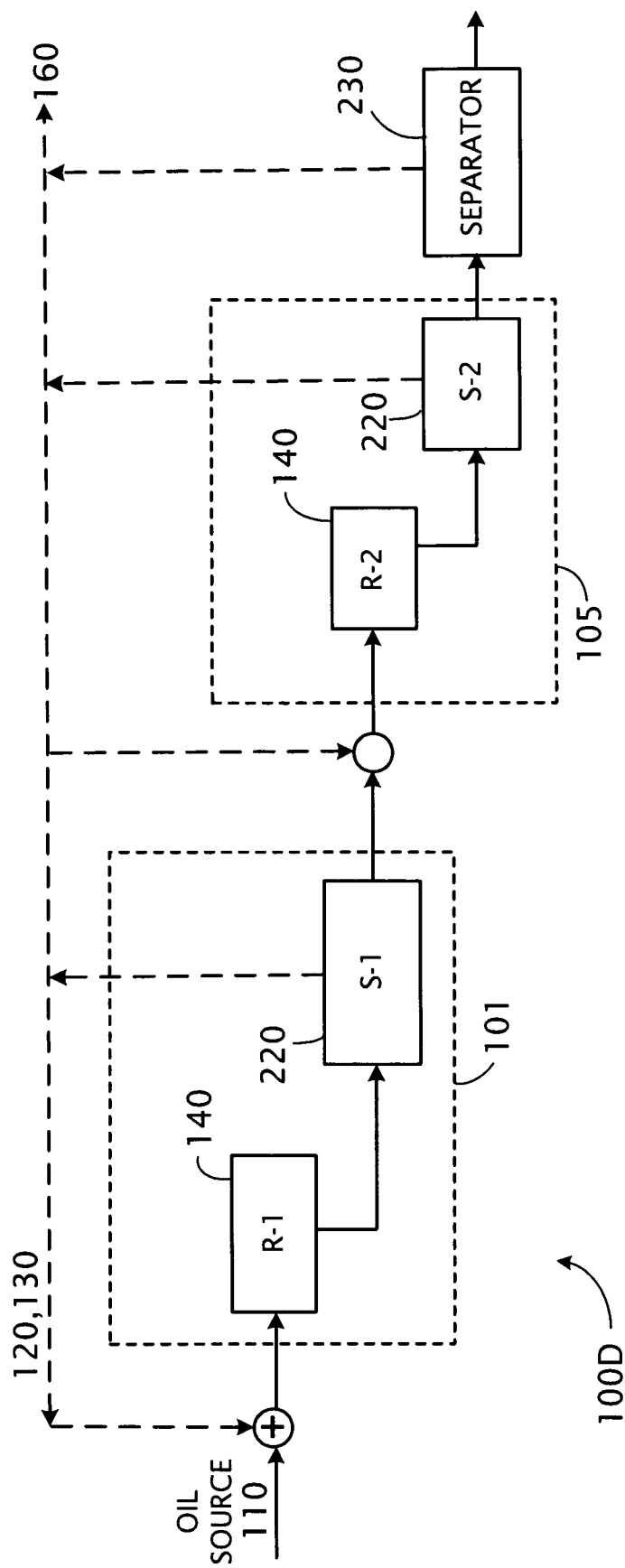

Referring to FIGS. 2C-D, plants that do not make use of feedback of crude bio-diesel have configurations that are otherwise similar to the plants shown in FIGS. 2A-B, respectively. As examples, the outputs of the first separators 220 in these versions of the plant are at least 80% pure, and in the two-stage version shown in FIG. 2D, the output of the second separator is at least 95% pure.

The single-stage plant 100C is useful, for example, when the catalyst (such as a particular type of lipase) is expensive, and the end product has high added value, such as for medical or drug use. The amount of lipase that is required in the single-stage plant 100C may be less than that of the double-stage plants 100B and 100D, and thus the end product can be produced more cost efficiently.

The plants 100A to 100D can have various configurations. Additional components may be included in the plants, such as heat exchangers to increase or decrease the temperatures of the solutions, and pumps to control the flow of the solutions. Removal beds may be included to remove unwanted moisture, glycerol, or other unwanted impurities from the products. For example, in the single-stage plant 100A, the separator 230 can separate non-completely reacted raw material (for example, reactant and oil source) from the product, so that the non-completely reacted raw material can be recycled. In this case, a glycerol removal bed filled with ion exchange resin can be used to remove trace glycerol from the recycled raw material.

In some examples, when certain types of enzymatic catalyst are used, for example, *thermomyces lanuginosa* lipase, it is useful to limit the amount of moisture in the solution flowing into the reactor 140. In such cases, a cartridge type water removal bed filled with moisture adsorption (or absorption) resin can be employed at the oil feedstock inlet stream for smaller plants. For larger plants, water moisture can be controlled by other removal techniques, such as evaporation or hot dry air stripping apparatus.

In some examples of the two-stage plants (for example, 100B and 100D), the final separator 230 can be omitted.

In the plants 100A to 100D, the reaction equilibrium in the reactors 140 can be determined by thermodynamics, and is independent of the type of enzymatic catalyst used. Thus, the concentration of biodiesel at equilibrium is a function of temperature, inert solvent concentration, reactant concentrations, and product concentrations. Different biodiesel equilibrium concentrations can be obtained at different temperatures when other conditions remain the same.

1.2 Chemical Configurations

A variety of combinations of oil sources, inert solvents, reactants, and catalysts, and associated operating conditions including temperature and reaction times, suitable for versions of the fuel production plants are described in U.S. application Ser. No. 10/945,339, filed Sep. 20, 2004, titled "Methods for Producing Alkyl Esters," to Chih-Chung Chou, which is incorporated by reference.

The processing approach is based on the discovery that high purity alkyl esters can be readily produced from an oil feedstock (for example, vegetable oils or animal fats) by a lipase-catalyzed reaction, in which inactivation of lipases is minimized. In particular, an alkyl ester can be produced, for example, via a transesterification or esterification reaction. The method includes (1) mixing an oil source containing a triglyceride or a carboxylic acid and a first primary alcohol or a first secondary alcohol in a first organic solvent to form a first solution; in which each molecule of the first organic solvent contains 4-8 carbon atoms and a heteroatom; (2) reacting the triglyceride or the carboxylic acid with the first primary alcohol or the first secondary alcohol in the presence of a first lipase to produce a first alkyl ester, in which the first solution does not undergo phase separation throughout the reaction; and (3) separating the first alkyl ester from the first solution.

Examples of a suitable oil source include plant oil (for example, microalgae oil), animal oil (for example, fish oil, lard, rendered fats, or tallow), waste grease (for example, waste restaurant grease), or a hydrolytic fraction thereof (for example, carboxylic acids). Before the mixing step, the oil source can be heated to 150-215° C. and cooled down to the reaction temperature.

Before the reaction, the oil source can be mixed with the first primary alcohol or the first secondary alcohol in the first organic solvent to form a one-phase solution. Examples of the first primary and secondary alcohols include those containing 1 to 18 carbon atoms, such as, methanol, ethanol, isopropanol, isobutanol, 3-methyl-1-butanol, hexanol, octanol, decanol, or lauryl alcohol. Examples of the first organic solvent include pyridine or a C4-C8 tertiary alcohol (for example, t-butanol, 2-methyl-2-butanol, 2,3-dimethyl-2-butanol, 2-methyl-2-pentanol, 3-methyl-3-pentanol, 3-ethyl-3-pentanol, 2,3-dimethyl-2-pentanol, 2,3-dimethyl-3-pentanol, 2,2,3-trimethyl-3-pentanol, 2-methyl-2-hexanol, or 3-methyl-3-hexanol). The first organic solvent can also be mixed with other suitable solvents. Preferably, the first organic solvents can be mixed with an alkyl ester, which can be an alkyl ester obtained from the method of this invention or an alkyl ester obtained from other sources (for example, purchased from a commercial source). When the first organic solvent is used together with another solvent, it is added in an amount sufficient to maintain the homogeneity of the first solution during the reaction, thereby minimizing the inactivation of the first lipase. The term "lipase" refers to any enzyme capable of catalyzing a transesterification or esterification reaction. Examples include *candida antarctica* lipase, *thermomyces lanuginosa* lipase, *pseudomonas fluorescens* lipase, *pseudomonas cepacia* lipase, or *chromobacterium viscosum* lipase. The first lipase can include a single lipase or a combination of two or more lipases. It is preferably immobilized on a carrier in the first reactor. The transesterification or esterification reaction can be carried out at 0-95° C. (for example, 20-95° C.) for 1-180 minutes (for example, 10-90 minutes or 20-60 minutes) to obtain the first alkyl ester.

During a transesterification reaction between an oil source containing a triglyceride and a first primary or secondary alcohol, glycerol is produced as a by-product. Unexpectedly, the first alkyl ester can be easily obtained by phase separation between the first alkyl ester and the glycerol after removing the first organic solvent and the unreacted first primary or secondary alcohol by evaporation. The just-mentioned oil source may also contain monoglycerides, diglycerides, or carboxylic acids. Monoglycerides and diglycerides react with the first primary or secondary alcohol in a manner similar to triglyceride. The carboxylic acids react with the first primary or secondary alcohol via an esterification reaction, in which water is produced as a by-product and can be readily removed during the evaporation process.

During an esterification reaction between an oil source containing a carboxylic acid and a first primary or secondary alcohol, water (but no glycerol) is produced as a by-product. It is also unexpected that the first alkyl ester can be easily obtained by removing the first organic solvent, the unreacted first primary or secondary alcohol, and the water by evaporation. When the just-mentioned oil source contains a significant amount of triglycerides, diglycerides, or monoglycerides, the first alkyl ester can be obtained in the manner described in the preceding paragraph.

If the first alkyl ester obtained above is contaminated with monoglycerides, diglycerides, triglyceride, or carboxylic acid, the contaminants can be removed by further reacting with an alcohol via another transesterification or esterification reaction. Specifically, the first alkyl ester can be mixed with a second primary alcohol or a second secondary alcohol in a second organic solvent to form a second solution. Each molecule of the second organic solvent contains 4-8 carbon atoms and a heteroatom. The second organic solvent can be the same or different from the first organic solvent. The second primary or secondary alcohol is preferably the same as the first primary or secondary alcohol. The monoglycerides, diglycerides, triglyceride, or carboxylic acid in the second solution can then react with the second primary alcohol or the second secondary alcohol in the presence of a second lipase to produce a second alkyl ester. In the reaction, the second solution does not undergo phase separation. The second lipase can be the same or different from the first lipase. The first and second alkyl esters thus obtained can then be separated from the second solution. Preferably, the second alkyl ester is identical to the first alkyl ester.

A number of examples of the processing approach are described below.

1.2.1 EXAMPLE 1

Soybean oil was used as an oil source for preparing alkyl esters. Specifically, refined soybean oil (55.4 wt %) was mixed with anhydrous methanol (8.6 wt %), and anhydrous t-butanol (36.0 wt %) in a first mixer to form a one-phase solution. The solution was then sent to a first reactor, which was filled with NOVOZYM 435 (a *candida antarctica* lipase; Novozymes A/S, Bagsvaerd, Denmark). Specifically, NOVOZYM 435 was immobilized on a carrier (a macroporous resin) and was then placed in the reactor. The temperature of the reactor was 45° C. The reaction time was 62 minutes. After the reaction was completed, the solution was fed into a vacuum evaporator and then a liquid-liquid separator to obtain a product. The composition of the product was determined by HPLC (column: Luna Su C18(2) 250×4.6 mm, phenomenex; mobile phases: methanol, hexane, and isopropanol; UV detector: UV-2075, JASCO, Japan). Unexpectedly, the product obtained contained 96.19 wt % alkyl esters, 3.59 wt % monoglycerides and diglycerides, and 0.22 wt % triglycerides.

In another experiment, an alkyl ester was used as a co-solvent. Specifically, refined soybean oil (49.1 wt %) was mixed with anhydrous methanol (7.6 wt %), anhydrous t-butanol (20.5 wt %), and an alkyl ester (22.8 wt %) in a first mixer to form a one-phase solution. The reaction conditions were the same as those described above except that the reaction completed in 58.0 minutes. Unexpectedly, the product obtained contained 96.10 wt % alkyl esters, 3.23 wt % monoglycerides and diglycerides, and 0.67 wt % triglycerides.

In still another experiment, t-amyl alcohol and an alkyl ester were used as solvents. Specifically, refined soybean oil (40.8 wt %) was mixed with anhydrous methanol (6.3 wt %), anhydrous t-amyl alcohol (37.3 wt %), and an alkyl ester (15.6 wt %) in a first mixer to form a one-phase solution. The reaction conditions were the same as those described above except that the reaction completed in 53.0 minutes. Unexpectedly, the product obtained contained 96.96 wt % alkyl esters, 2.64 wt % monoglycerides and diglycerides, and 0.40 wt % triglycerides.

1.2.2 EXAMPLE 2

An alkyl ester obtained from Example 1 was mixed with anhydrous methanol and anhydrous t-butanol in another mixer to form a one-phase solution. The solution thus formed contained 70.00 wt % of the alkyl ester, 2.8 wt % of contaminants (i.e., 2.47 wt % of monoglycerides and diglycerides and 0.31 wt % of triglycerides), 7.28 wt % of the methanol, and 19.94 wt % of the t-butanol. The solution was then sent to another reactor, which was filled with NOVOZYM 435. Specifically, NOVOZYM 435 was immobilized on a carrier and then placed in the reactor. The temperature of the second reactor was 45° C. The reaction time was 17.5 minutes. After the reaction was completed, the solution was fed into another vacuum evaporator and then another liquid-liquid separator to obtain a product. The composition of the product was determined by HPLC.

Unexpectedly, the product obtained above contained 99.24 wt % alkyl esters, 0.65 wt % monoglycerides and diglycerides, and 0.11 wt % triglycerides.

1.2.3 EXAMPLE 3

Oil sources other than soybean oil were used as starting materials for preparing alkyl esters in a manner similar to that described in Example 1. Oil sources used included waste restaurant grease containing high free fatty acids, waste restaurant grease containing low free fatty acids, tallow, lard, fish oil, palm oil, and castor oil. In one experiment, waste restaurant grease containing high free fatty acids was used. Specifically, the reactor containing NOVOZYM 435 was fed with a solution containing such waste restaurant grease (49.1 wt %), anhydrous methanol (7.6 wt %), t-butanol (20.5 wt %), and an alkyl ester (22.8 wt %). Specifically, NOVOZYM 435 was immobilized on a carrier and then placed in the reactor. The temperature of the reactor was 45° C. The reaction time was 24.0 minutes. The product from the reactor was isolated and its composition was determined by HPLC. Unexpectedly, the product obtained above contained 96.63 wt % alkyl esters, 3.17 wt % monoglycerides and diglycerides, and 0.20 wt % triglycerides.

In another experiment, fish oil (an animal oil) was used as an oil source. Specifically, fish oil (52.4 wt %) was mixed with anhydrous methanol (7.8 wt %), and anhydrous pyridine (39.8 wt %) in a first mixer to form a one-phase solution. The reaction conditions were the same as those described above except that the reaction completed in 25.0 minutes. Unexpectedly, the product obtained contained 95.63 wt % alkyl esters, 3.03 wt % monoglycerides and diglycerides, and 1.34 wt % triglycerides.

In still another experiment, palm oil (a plant oil) was used as an oil source. Specifically, plant oil (46.5 wt %) was mixed with anhydrous methanol (7.5 wt %), and anhydrous t-amyl alcohol (46.0 wt %) in a first mixer to form a one-phase solution. The reaction conditions were the same as those described above except that the reaction completed in 41.0 minutes. Unexpectedly, the product obtained contained 96.97 wt % alkyl esters, 1.95 wt % monoglycerides and diglycerides, and 1.08 wt % triglycerides.

1.2.4 EXAMPLE 4

Primary alcohols were used as starting materials for preparing alkyl esters in a manner similar to that described in Example 1. Alcohols used included methanol, ethanol, isobutanol, 3-methyl-1-butanol, hexanol, octanol, decanol, and lauryl alcohol. In one experiment, the reactor containing NOVOZYM 435 was fed with a solution containing fish oil (52.0 wt %), ethanol (11.2 wt %), and anhydrous t-butanol (36.8 wt %). Specifically, NOVOZYM 435 was immobilized on a carrier and then placed in the reactor. The temperature of the reactor was 45° C. The reaction time was 39.0 minutes. The product from the reactor was isolated and its composition was determined by HPLC. Unexpectedly, the product obtained above contained 97.44 wt % alkyl esters, 1.44 wt % monoglycerides and diglycerides, and 1.11 wt % triglycerides.

In another experiment, hexanol (a C6 alcohol) was used as a starting material. Specifically, soybean oil (53.7 wt %) was mixed with anhydrous hexanol (26.6 wt %), and anhydrous t-butanol (19.7 wt %) in a first mixer to form a one-phase solution. The reaction conditions were the same as those described above except that the reaction completed in 46.0 minutes. Unexpectedly, the product obtained contained 95.06 wt % alkyl esters, 4.11 wt % monoglycerides and diglycerides, and 0.88 wt % triglycerides.

In still another experiment, lauryl alcohol (a C12 alcohol) was used as a starting material. Specifically, soybean oil (37.2 wt %) was mixed with anhydrous lauryl alcohol (33.6 wt %), and anhydrous t-butanol (29.2 wt %) in a first mixer to form a one-phase solution. The reaction conditions were the same as those described above except that the reaction completed in 66.0 minutes. Unexpectedly, the product obtained contained 95.03 wt % alkyl esters, 4.07 wt % monoglycerides and diglycerides, and 0.90 wt % triglycerides.

1.2.5 EXAMPLE 5

Secondary alcohols were used as starting materials for preparing alkyl esters in a manner similar to that described in Example 1. Alcohols used included isopropanol (a C3 alcohol), 2-butanol (a C4 alcohol), and secondary n-octyl alcohol (a C8 alcohol). In one experiment, the reactor containing NOVOZYM 435 was fed with a solution containing rapeseed oil (52.9 wt %), isopropanol (14.1 wt %), and anhydrous t-amyl alcohol (33.0 wt %). Specifically, NOVOZYM 435 was immobilized on a carrier and then placed into the reactor. The temperature of the reactor was 45° C. The reaction time was 39.0 minutes. The product from the reactor was isolated and its composition was determined by HPLC. Unexpectedly, the product obtained above contained 93.92 wt % alkyl esters, 4.86 wt % monoglycerides and diglycerides, and 1.22 wt % triglycerides.

In another experiment, 2-butanol was used as a starting material. Specifically, soybean oil (52.5 wt %) was mixed with anhydrous 2-butanol (18.9 wt %), and anhydrous t-amyl alcohol (28.6 wt %) in a first mixer to form a one-phase solution. The reaction conditions were the same as those described above except that the reaction completed in 46.0 minutes. Unexpectedly, the product obtained contained 92.84 wt % alkyl esters, 5.08 wt % monoglycerides and diglycerides, and 2.09 wt % triglycerides.

In still another experiment, secondary n-octyl alcohol was used as a starting material. Specifically, soybean oil (46.4 wt %) was mixed with anhydrous secondary n-octyl alcohol (29.3 wt %), and anhydrous t-butanol alcohol (24.3 wt %) in a first mixer to form a one-phase solution. The reaction conditions were the same as those described above except that the reaction completed in 42.0 minutes. Unexpectedly, the product obtained contained 94.69 wt % alkyl esters, 2.45 wt % monoglycerides and diglycerides, and 2.86 wt % triglycerides.

1.2.6 EXAMPLE 6

An alkyl ester was prepared using lauric acid and methanol as starting materials via an esterification reaction in a manner similar to that described in Example 1. Specifically, the reactor containing NOVOZYM 435 was fed with a solution containing anhydrous lauric acid (77.7 wt %), anhydrous methanol (17.6 wt %), and anhydrous t-butanol (4.7 wt %). NOVOZYM 435 was immobilized on a carrier and then into the reactor. The temperature of the reactor was 45° C. The reaction time was 37.0 minutes. The product from the reactor was isolated and its composition was determined by GC (8610C, SRI, USA; column: MXT-65TG, length: 30 m, I.D.: 0.25 µm; carrier gas: He, flow rate: 1 ml/min; injector: split ratio: 20 to 1, temperature: 300° C.; detector: FID, temperature: 370° C.).

Unexpectedly, the product obtained above contained 96.0 wt % methyl laurate and 4.0 wt % lauric acid.

1.2.7 EXAMPLE 7

Alkyl esters were prepared using soybean oil and methanol as starting materials in a manner similar to that described in Example 1 except that the soybean oil was heated for a period of time before use. Specifically, the soybean oil was first heated either at 200° C. for 5 minutes or at 210° C. for 1 hour and then cooled down to the reaction temperature. Subsequently, the soybean oil (49.1 wt %) was mixed with anhydrous methanol (7.6 wt %), anhydrous t-butanol (20.5 wt %), and an alkyl ester (22.8 wt %) in the mixer to form a one-phase solution. The solution was then sent to the reactor, which was filled with NOVOZYM 435. Specifically, NOVOZYM 435 was immobilized on a carrier and was placed into the reactor in advance. The temperature of the reactor was 45° C. Each product from the reactor was isolated and its composition was determined by HPLC.

Unexpectedly, it took 50.3 minutes and 47.4 minutes to obtain a product containing less than 1.5 wt % triglycerides using soybean oil heated at 200° C. for 5 minutes and using soybean oil heated at 210° C. for 1 hour, respectively. In comparison, it took 53.8 minutes to do so in a similar reaction condition using soybean oil without prior heat treatment.

1.2.8 EXAMPLE 8

LIPOZYME TL IM (a *thermomyces lanuginosa* lipase, Novozymes A/S, Bagsvaerd, Denmark) was used as a catalyst for preparing alkyl esters in a manner similar to that describe in Example 1. Specifically, it was immobilized on a granulated silica carrier and then placed in the reactor. The reactor was then fed with a solution containing soybean oil (49.1 wt %), anhydrous methanol (7.6 wt %), anhydrous t-butanol (20.5 wt %), and an alkyl ester (22.8 wt %). The temperature of the reactor was 45° C. The reaction time was 51.0 minutes. The product from the reactor was isolated and its composition was determined by HPLC.

Unexpectedly, the product obtained above contained 94.04 wt % alkyl esters, 3.65 wt % monoglycerides and diglycerides, and 2.31 wt % triglycerides.

2 Single-stage Biodiesel Fuel Production Approach

Figure 3:
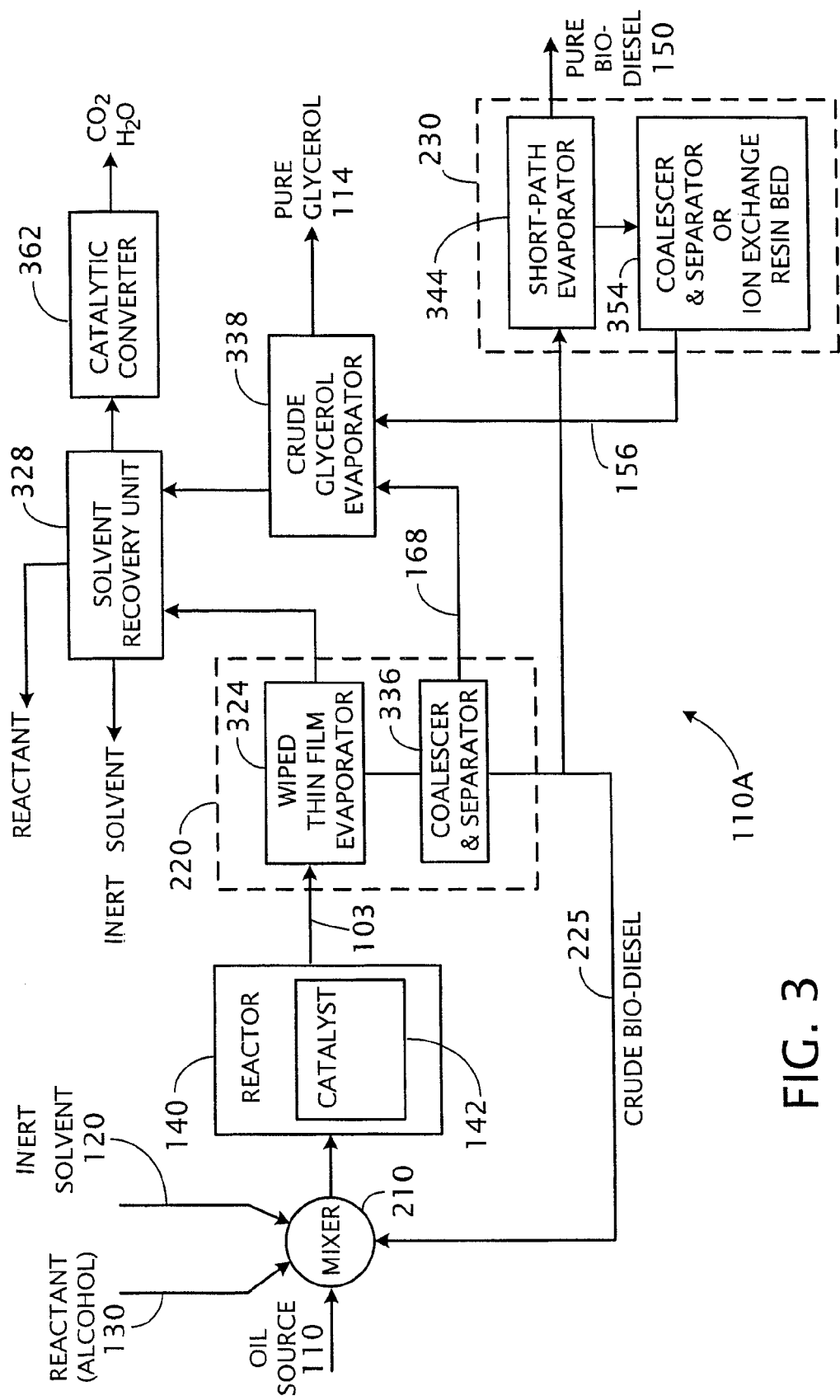
FIG. 3 is a block diagram of a single stage plant with feedback of crude bio-diesel.

Referring to FIG. 3, an example of the processing plant 100A of the configuration shown in FIG. 2A includes a number of components used to implement separators 220 and 230, as well as additional components not shown in FIG. 2A used to process the recovered output and waste products produced by the separators. In this example, the reactant 130 includes an alcohol.

The reactor 140 can be, for example, a plug flow reactor that includes the enzymatic catalyst 142. A description of the reaction between the oil source 110 and the reactant alcohol 130 can be found in section 1.2, and in U.S. patent application Ser. No. 10/945,339. The velocity of fluid flow through the reactor 140 is controlled so as to meet a residence time specified for the reactor 140, allowing sufficient time for the reactions to be completed. The residence time can range from, for example, 3 hours to less than 20 minutes. The temperature of the reactor 140 is maintained at a preset value, which can range from, for example, 20° C. to 95° C., depending in part on the type of oil source, reactant, and catalyst.

The reactor 140 outputs a crude product 103, which includes alkyl ester, glycerol, and impurities, such as uncompleted reacted oils that are generated from the reaction between the oil source 110 and the reactant 130. Examples of uncompleted reacted oils include monoglyceride and diglyceride.

The processing plant 100A includes a separation module 220 that separates the components in the crude product 103 into, for example, crude glycerol 168 and crude biodiesel 150 including unreacted oil 110, inert solvent 120, and unreacted reactant 130. The separation module 220 includes a vacuum evaporator, such as a wiped thin film evaporator 324, model VD type, made by Verfahrens Technische Aulagen GMBH, Deggendorf, Germany, or a simple flash drum integrated with a packed bed evaporator. The thin film evaporator 324 separates the various components in the crude product 103 using thin film evaporation. The thin film evaporator 324 includes a thin film that has a large surface area so that the inert solvent 120, unreacted alcohol 130, and water can be evaporated at a faster rate. Components having lower boiling points, such as unreacted alcohol 130, water vapor, inert solvent, and other impurities, are flashed, condensed, and collected in a solvent recovery unit 328, which separates the inert solvent 120, the unreacted alcohol 130, water vapor, and other impurities. The inert solvent 120 and the unreacted alcohol 130 can be recycled and mixed with fresh solvent 120, fresh oil source 110, and fresh reactant alcohol 130 as part of the input to the reactor 140. The water vapor and other impurities are sent to a catalyst converter 362, which coverts the impurities into, for example, carbon dioxide. The water vapor and the carbon dioxide are output through a vent (not shown).

Residue from the thin film evaporator 324 includes glycerol, alkyl ester, unreacted oil, and uncompleted reacted oil, which are sent to a first coalescer and separator 336. The coalescer coalesces the glycerol droplets into liquid form. After the solution settles down for a period of time in the separator, the biodiesel and the glycerol will be separated, forming an upper layer of biodiesel and a lower layer of glycerol.

The lower layer of glycerol is referred to as crude glycerol 168, which includes impurities, such as water, inert solvent, and unreacted alcohol. The crude glycerol 168 is sent to a crude glycerol evaporator 338. An example of the evaporator 338 is a short-path evaporator, such as model VK type, made by VTA GMBH, or a simple flash drum coupled with a packed bed evaporator. The evaporator 338 operates by evaporation to separate the glycerol from impurities, and outputs the "pure" glycerol 114. As an example, the pure glycerol 114 can be at least 99% pure by weight.

The upper layer of biodiesel is referred to as crude biodiesel 225 because it includes impurities, such as uncompleted reacted oil, unreacted oil, and trace amount of glycerol. A portion of the crude biodiesel 225 is recycled and fed back to the reactor 140. As described above, recycling the crude biodiesel 225 can reduce the amount of inert solvent that is required for dissolving the oil source and reactant alcohol, in addition to the advantage of promoting the reaction to completeness.

The portion of the crude biodiesel 225 that is not recycled is sent to the final separator 230, which includes a short-path evaporator 344 that separates the biodiesel from the impurities to generate the pure biodiesel 150.

The short-path evaporator 344 outputs uncompleted oil, unreacted oil, and glycerol to a second coalescer and separator 354 or a regeneratable ion exchange resin bed (plug flow bed), which separates or removes the glycerol from the other components. The coalescer and separator 354 outputs crude glycerol 156 to the crude glycerol evaporator 338, which processes the crude glycerol 156 to generate pure glycerol 114. The coalescer and separator 354 outputs uncompleted and unreacted oils, which, optionally, can be recycled and fed back to the reactor 140.

3 Detailed Design of a Single-stage System

Figure 4:
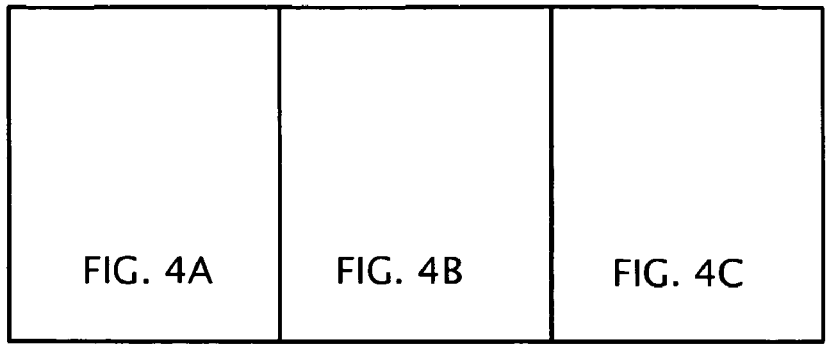
FIG. 4 is a schematic diagram of a single stage plant with feedback of crude bio-diesel.

Referring to FIG. 4, another example of plant 110A of the configuration shown in FIG. 2A is described in detail below.

Referring to FIG. 4, the plant 10A includes an oil drum (D-1) that stores the oil source 110. The inert solvent 120 is stored in a solvent drum, which receives fresh inert solvent, recycled inert solvent from solvent recovery unit within the plant, and nitrogen gas. The nitrogen gas blocks out moisture and oxygen from the solvent. The reactant alcohol 130 is stored in a reactant alcohol drum, which receives fresh reactant alcohol, recycled reactant alcohol, and nitrogen gas.

Mixing of the oil source 110, inert solvent 120, and reactant alcohol 130 is performed using a number of components. A twin headed metering pump (P-1) 430 pumps the oil source 110 along a path 432 at a fixed rate towards a water removal bed (RB-1) 436, which can be, for example, a packed bed filled with super-absorbent polymer that removes trace water directly from the oil source. After the water is removed, the oil source is sent through a pipe 440 toward the mixer 210, which includes a static mixer (SM-1) 438. At the same time, a twin headed metering pump (P-2) 424 pumps the reactant and the inert solvent toward the static mixer 438 at a rate so that the ratio of oil source versus the reactant alcohol and inert solvent is maintained at a predetermined value. The pump 430 also pumps recycled crude bio-diesel 225 through a pipe 476 toward the static mixer 438, at a predetermined ratio of recycled crude biodiesel verse oil source.

The static mixer 438 can be, for example, a multi-element static mixer such as described in U.S. Pat. No. 3,286,992, or a compact mixer, such as Sulzer Compact Static Mixer, available from Sulzer Chemtech, Switzerland. A static mixer does not have moving parts, and mixes the solution without external power. The static mixer 438 causes the reactant, the inert solvent, the oil source and the recycled crude bio-diesel to mix thoroughly to produce a homogeneous solution.

The reactor 140, which includes a heat exchanger (HE-1) 448 and a cartridge type reactor (R-1) 404, receives the output of the mixer 210. Specifically, the output of static mixer 438 is forwarded to a heat exchanger (HE-1) 448, which regulates the temperature of the mixed solution by using, for example, cooling water, hot oil, steam, or electrical heaters or coolers. The heat exchanger 448 can have, for example, a double pipe design. The solution then enters an elongated cartridge 404 of the reactor that is filled with the enzymatic catalyst 142, in this case lipase. The reaction temperature can be in a range of 0 to 95° C., preferably at room temperature (for example, 25° C.).

A number of alternative types of cartridge 404 can be used. For example, the cartridge 404 can be a column with grid support at the bottom. A screen is provided at the bottom of the cartridge to retain the enzymatic catalyst 142 within the cartridge, and another screen is provided at the upper portion of the cartridge to level a flow of the solution in the cartridge. Between the two screens, the cartridge is filled with the catalyst. The temperature-regulated mixed solution enters the cartridge 404 through an opening on the top of the cartridge, and flows down through the enzymatic catalyst 142. The enzymatic catalyst facilitates a reaction between the reactant alcohols and the oil source, which includes triglyceride, to generate alkyl ester, glycerol, and water (and/or other impurities).

The reactor 140 outputs a crude product that includes alkyl ester, glycerol, unreacted oil (triglyceride), uncompleted oil (monoglyceride and diglyceride), unreacted alcohol, inert solvent, and other impurities. As described above with reference to FIG. 3, the crude output of the reactor 140 is passed to a separator 220, which includes an evaporator 324 and coalescer and separator 336. In FIG. 4, a particular design of coalescer and separator 336 is indicated by reference numeral 336A, in which a membrane filter with pore size 1~5 µm is employed for coalescing of glycerol droplets.

In the plant 110A shown in FIG. 4, the evaporator 324 includes a pressure regulator (PR) 452, a preheater (HE-2) 448, and an evaporator of simple flash drum integrated with a packed bed design (E-1) 451. The preheater 448 can use, for example, hot oil or steam to pre-heat the crude product. The evaporator 451 can use hot oil or steam as a heating medium in the jacketed area. Inside the evaporator 451, inert solvent, water, and unreacted alcohol are evaporated and exit the evaporator 451 through an upper opening. The inert solvent, water, and the unreacted alcohol are condensed and collected in the solvent recovery unit 328 (not shown in FIG. 4), and can be recycled.

The composition of the condensate liquid in the solvent recovery unit may include unreacted alcohol, inert solvent, water and trace amount of biodiesel. Two simple columns can be used to separate the unreacted alcohol, inert solvent, and water. In one example, the first column separates the inert solvent from the unreacted alcohol and water. The inert solvent, including trace amount of biodiesel, if any, exits from the bottom of the first column and is recycled to the inert solvent drum.

In the solvent recovery unit, the unreacted alcohol and water exits from the top of the first column and are sent to the second column, where the unreacted alcohol is collected in a top reflux drum and recycled to the reactant alcohol drum. The bottom residue in the second column consists mostly of water and small amounts of unreacted alcohol and inert solvent. The small amount of unreacted alcohol and inert solvent can be vaporized through a catalyst converter and burned out completely. Both simple columns can be operated automatically at ambient pressure. In general, the design of solvent recovery depends on the alcohol and the inert solvent that are used, and different recovery schemes may be used.

Continuing to refer to FIG. 4, the components in the evaporator 451 having higher boiling points are pumped by a gear pump (p-6) to a coalescer (CL-1) 454, and the glycerol droplets coalesce into large droplets that can be easily separated from the crude biodiesel. Two liquids are formed in the liquid-liquid phase separator (S-2) 456. Crude biodiesel is sent through a cooler (HE-3) 458 and a trace glycerol removal bed (RB-3) 461, which is filled with a regeneratable ion exchange resin. The output of the trace glycerol removal bed 461 is split into two flows 476 and 478. One flow 476 is recycled to the static mixer 438, the other flow 478 is sent to the short-path evaporator (E-2) 424

Crude biodiesel, which may include at least 95% by weight of alkyl ester, flows out of the separator 456 and is cooled by a cooler (HE-3) 458. Cooling water is used to cool the crude biodiesel in the cooler.

A portion of the crude bio-diesel is recycled through a feed back pipe 476. The recycled crude biodiesel passes a three-way solenoid valve 478, which can switch between crude biodiesel and pure biodiesel. As described above, the pump 430 pumps the recycled biodiesel toward the static mixer 438.

The portion of the crude bio-diesel that is not recycled is sent to the short-path evaporator 344 (part of final separator 230 as shown in FIG. 3). The short path evaporator 344 includes a heat exchanger (HE-4) 486, a pressure regulator 452, and a short-path evaporator (E-2) 424. The short-path evaporator 424 separates the biodiesel from the glycerol, unreacted oil, and other impurities. High purity biodiesel flows out of the evaporator 424 through a path 426.

The evaporator 424 outputs unreacted oil contaminated with trace amount of glycerol through a path 433 to a drum (S-4) 472. The unreacted oil is pumped by a gear pump (P-8) 473 through a cooler (HE-6) 475. Depending on the quality of the unreacted oil and/or the amount of impurity in the oil, the unreacted oil can be sent to a waste oil disposal drum, or sent through a glycerol removal bed (RB-2) 444 to remove any remaining glycerol and recycled to the oil drum D-1. The glycerol removal bed 444 can be, for example, a packed bed filled with a resin that can remove traces of glycerol from the solution.

A dual gravity drain trap (DN-1) 457 is placed between the liquid-liquid phase separator (S-2) 456 and the drum 474 to discharge the glycerol automatically. An example of the trap 457 is available from Armstrong, Mich., U.S.A. Alternatively, if the drain trap cannot be used because the amount of glycerol is too small, a small drum with a high level switch and a low level switch, both coupled to a solenoid valve in the drum bottom for glycerol discharge, can be used.

The crude glycerol in the drum 474 can be refined through a vacuum evaporator (not shown in FIG. 4) to remove water, unreacted alcohol, and inert solvent. The evaporated vapor is condensed and lumped with the condensate liquid drum of evaporator E-1 (and E-2) described above. The residue leaving the crude glycerol evaporator is pure glycerol product suitable for commercial use.

High purity biodiesel from the short-path evaporator 424 is pumped through a heat exchanger (HE-5) 408, in which cooling water cools the high purity biodiesel. The final pure biodiesel product may include at least 99% by weight of alkyl ester. The pure biodiesel product is stored in a pure biodiesel product drum (D-5). During the start-up of the processing plant, the pure biodiesel can be recycled through a feedback path to the mixer 210 for the reactor 140 when the crude biodiesel is not available. The feedback path is connected to the solenoid valve 478 so that the recycled pure biodiesel can be switched off when the crude biodiesel is employed.

4 Alternative Design of a Single-stage System

Figure 5:
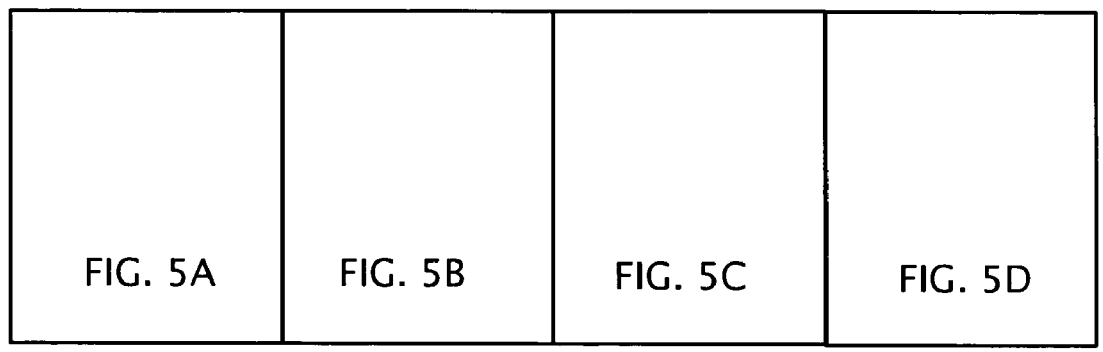
FIG. 5 is a schematic diagram of a single stage plant with feedback of crude bio-diesel.

FIG. 5 shows an alternative design of a single stage reactor that uses bottom product discharge design. Two liquid drums (S-1) 556 and (S-2) 566, which are switched between vacuum and atmosphere, are used to discharge liquid from a drum 455 coupled to the evaporator. Liquid detectors (not shown) are used in drums 556 and 566 for automatic control of switching operation for discharging liquids. Two-way solenoid valves 558 and 560, and a three-way solenoid valve 568 regulate the flow of the solution from the drum 455 to the drums 556 and 566. The valve 560 regulates a flow of liquid from the bottom of the drum 556. At a first time period, the valve 560 is closed, and the valve 558 is opened. The three-way solenoid valve 568 is configured so that a top opening of the drum 556 is coupled to a vacuum pump (not shown). The solution flows by gravity from the drum 455 into the drum 556.

After there is a preset amount of solution in the drum 556, the valve 558 is closed. The valve 560 is opened, and the 3-way solenoid valve 568 is selected so that room air can pass a silica gel (or resin) 570 and enter the top opening of the drum 556. The silica gel or resin 570 removes moisture from the air entering the drum 556.

Due to gravity, the solution in the drum 556 flows into the drum 566. After the solution flows out of the drum 556 to a preset level, the valve 560 is closed, the valve 568 is switched and valve 558 is reopened.

A pump 562 continuously pumps the solution through a coalescer (CL-1) 454, in which the glycerol droplets are coalesced into large droplets and separated from the crude biodiesel. The pump 562 functions similar to the role of gear pump 467 in FIG. 4. The difference is that, for the pump 562, the suction pressure is from ambient pressure instead of the high vacuum situation as in the case for the gear pump 467. This provides more flexibility in the selection of the pump, making it easier to find a suitable pump.

The downstream operation is similar to that given in FIG. 4. A similar design for the bottom flows of the short path evaporator (E-2) 424 can be employed.

5 Two-stage Plant

Figure 6:
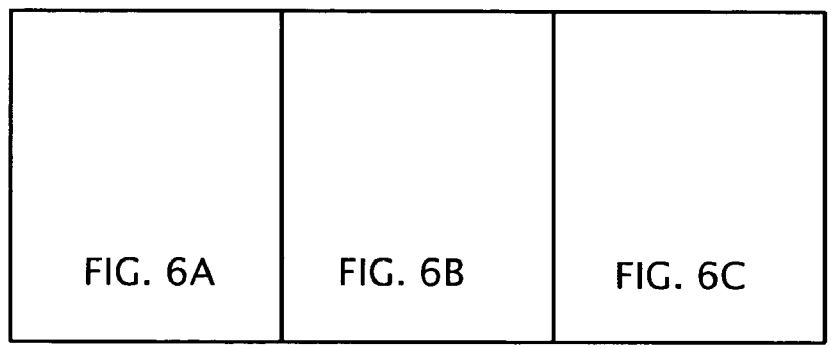
FIG. 6 is a schematic diagram of a two stage plant with feedback of crude bio-diesel.
Figure 4A:
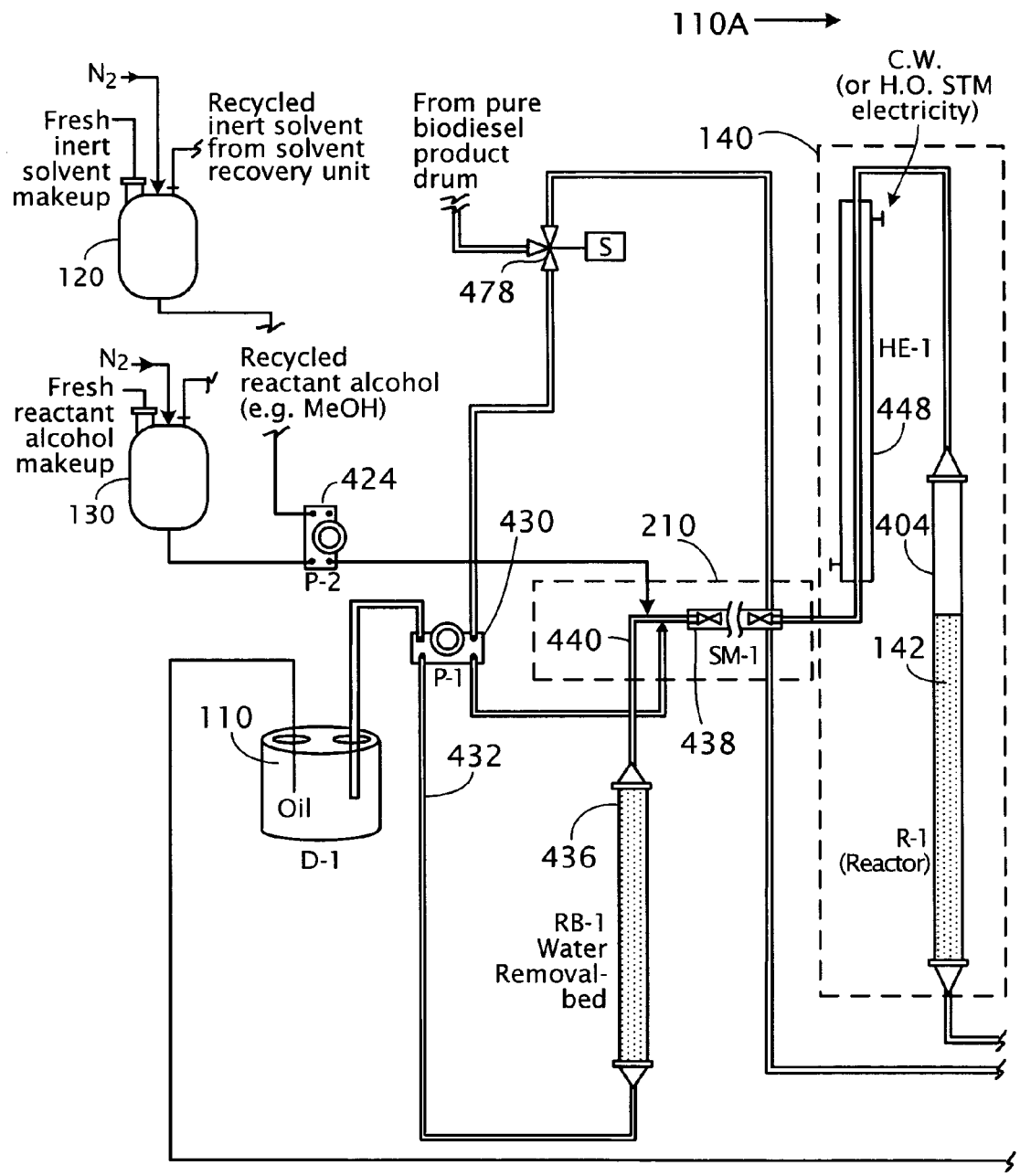
FIGS. 4A-C are enlarged views of portions of FIG. 4.
Figure 4B:
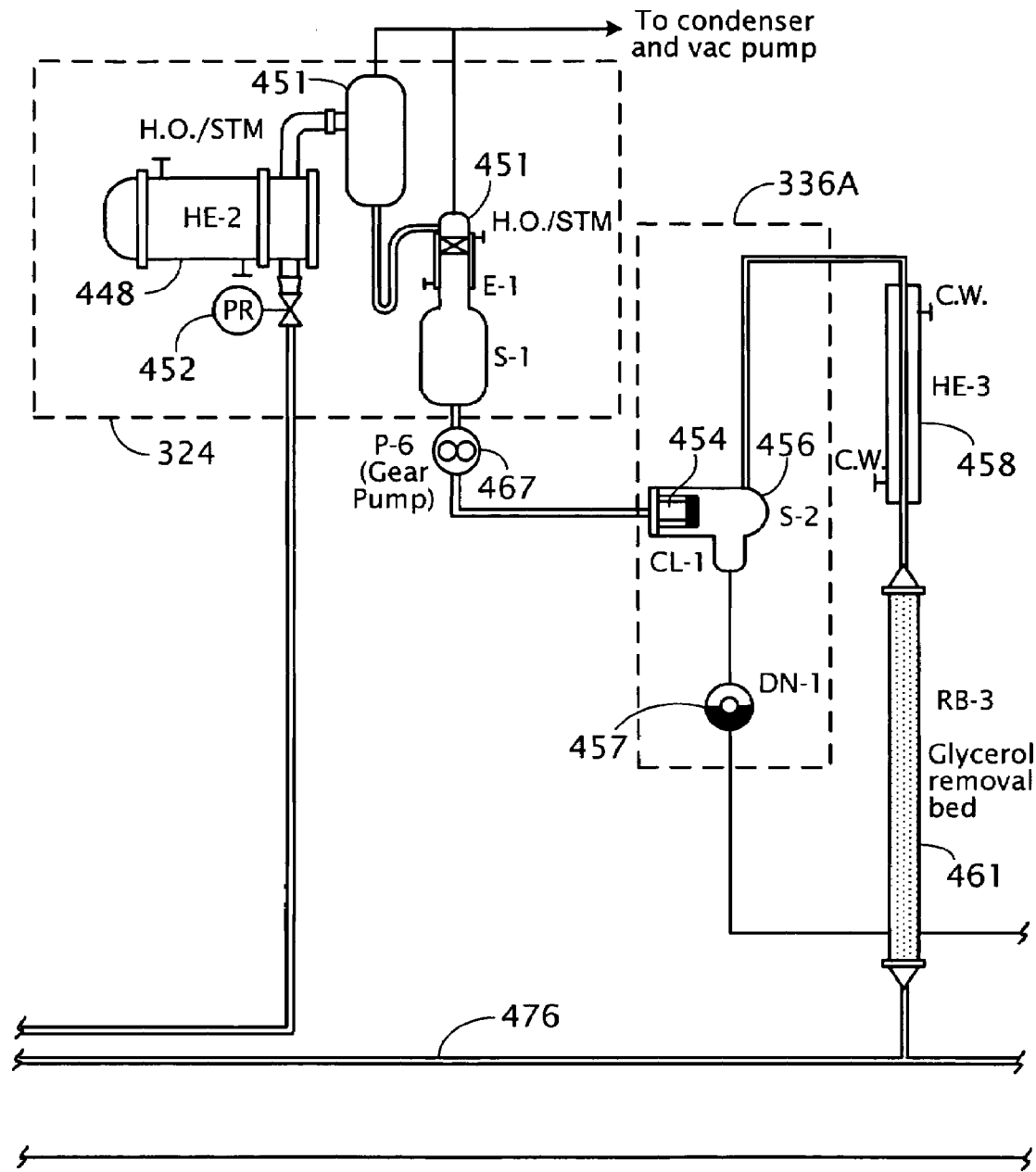
Figure 4C:
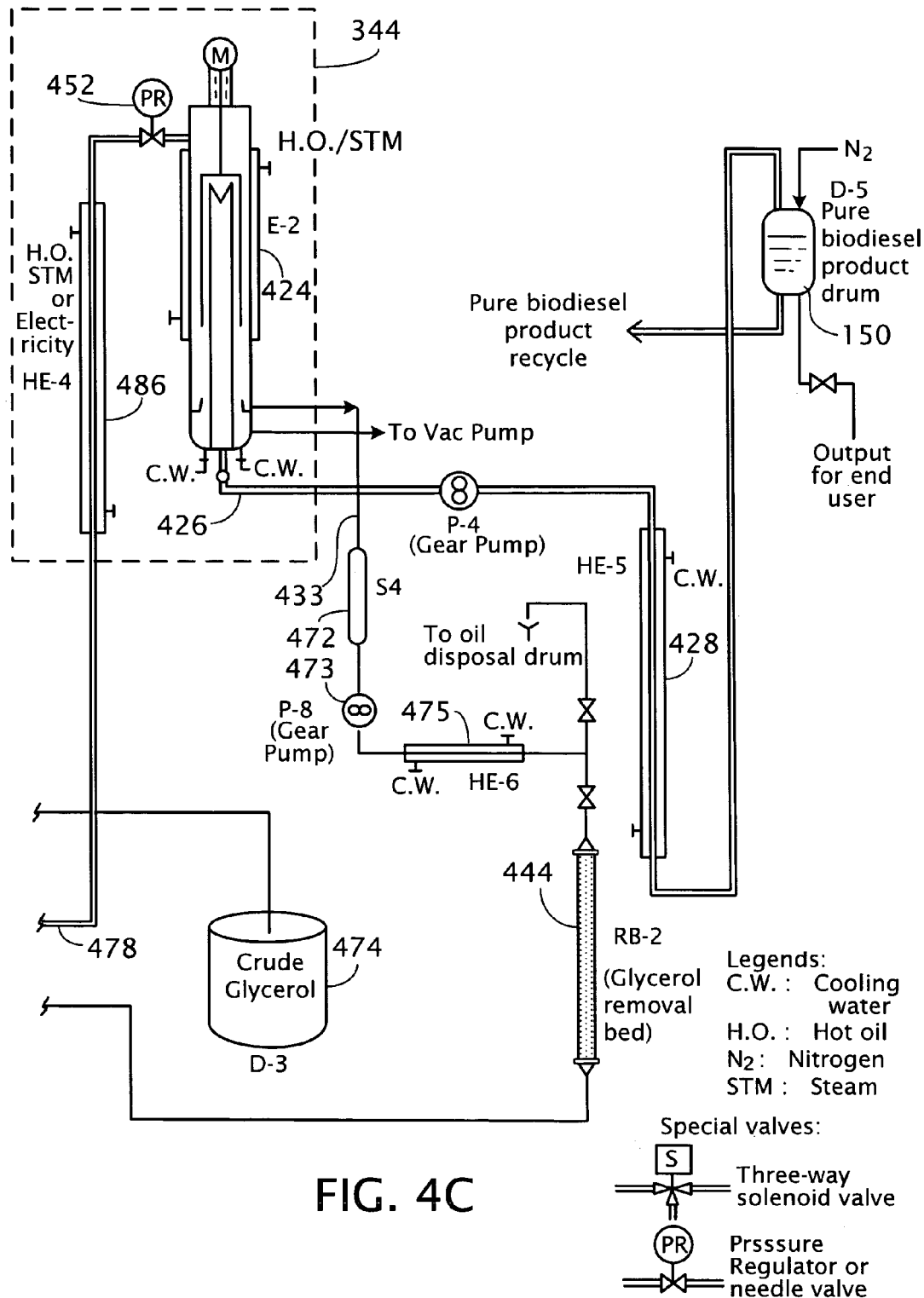
Figure 5A:
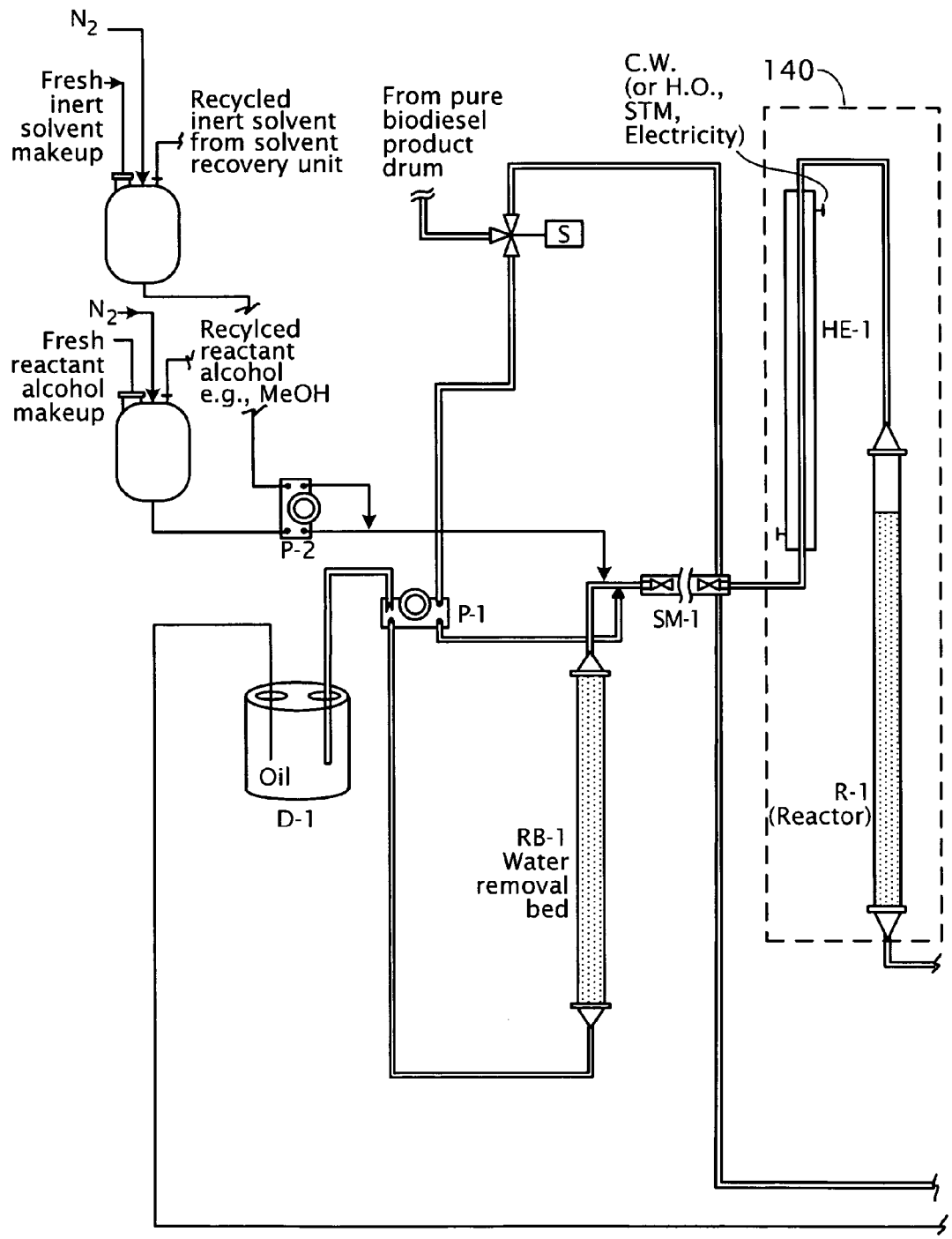
FIGS. 5A-D are enlarged views of portions of FIG. 5.
Figure 5B:
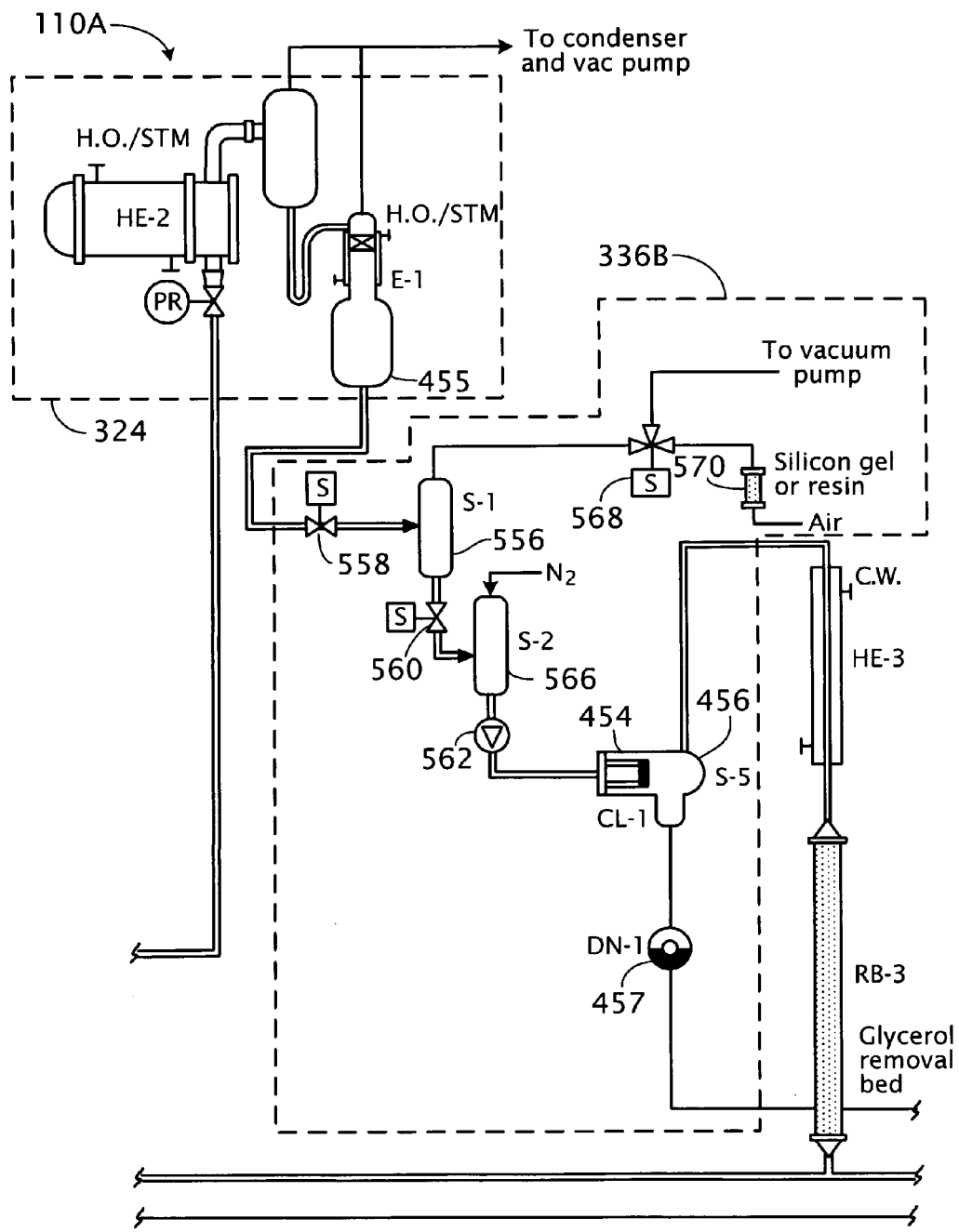
Figure 5C:
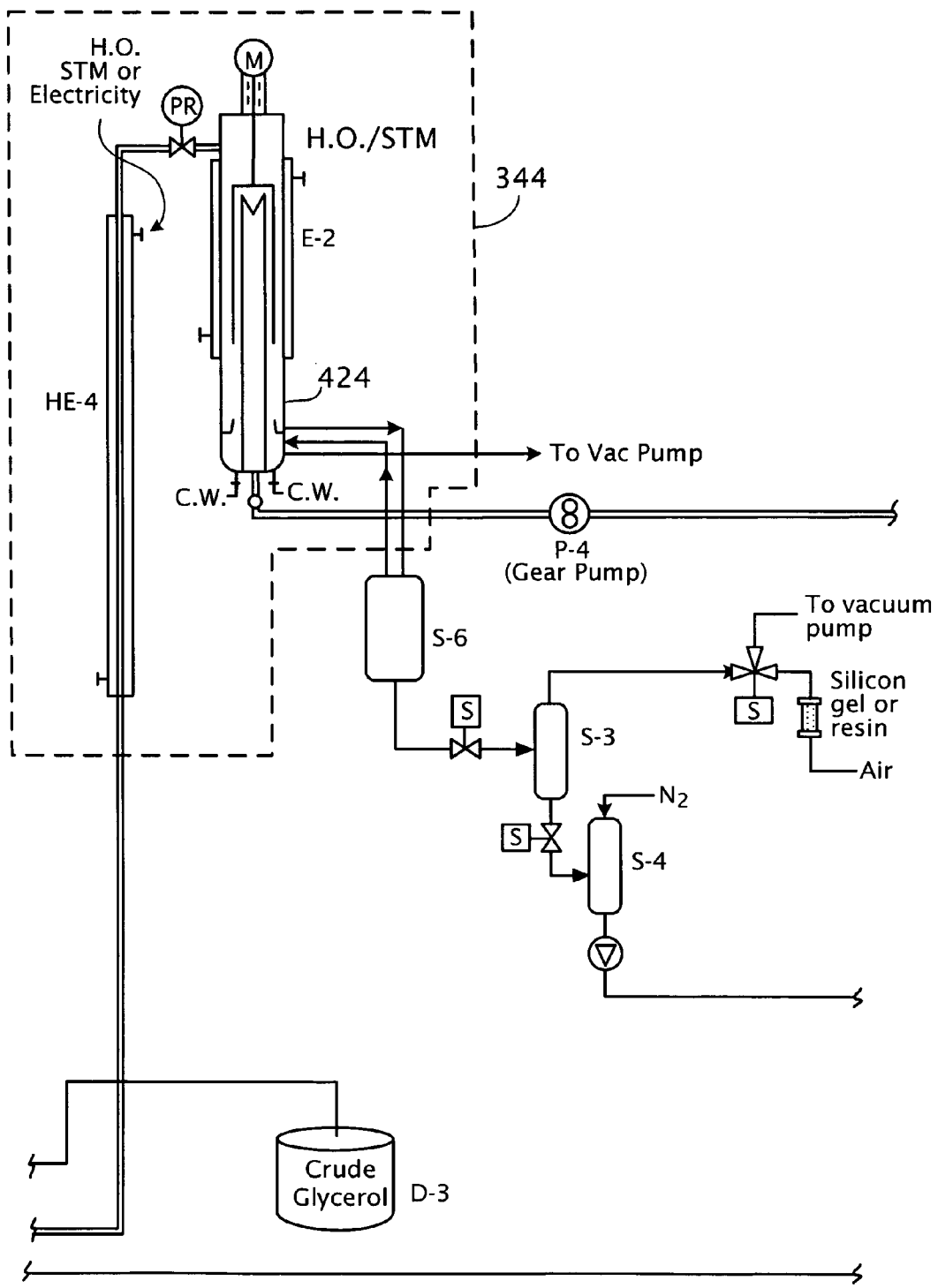
Figure 5D:
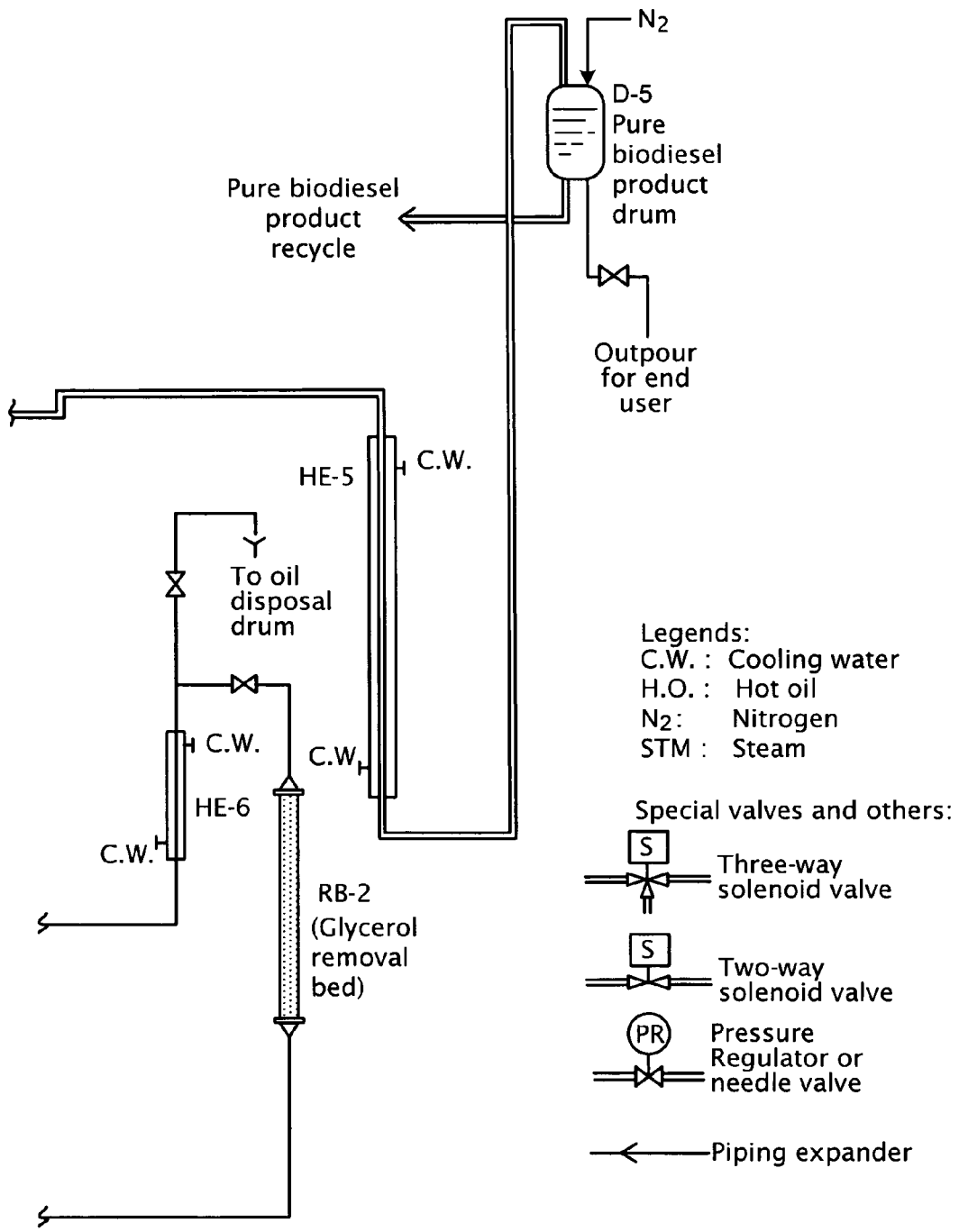
Figure 6A:
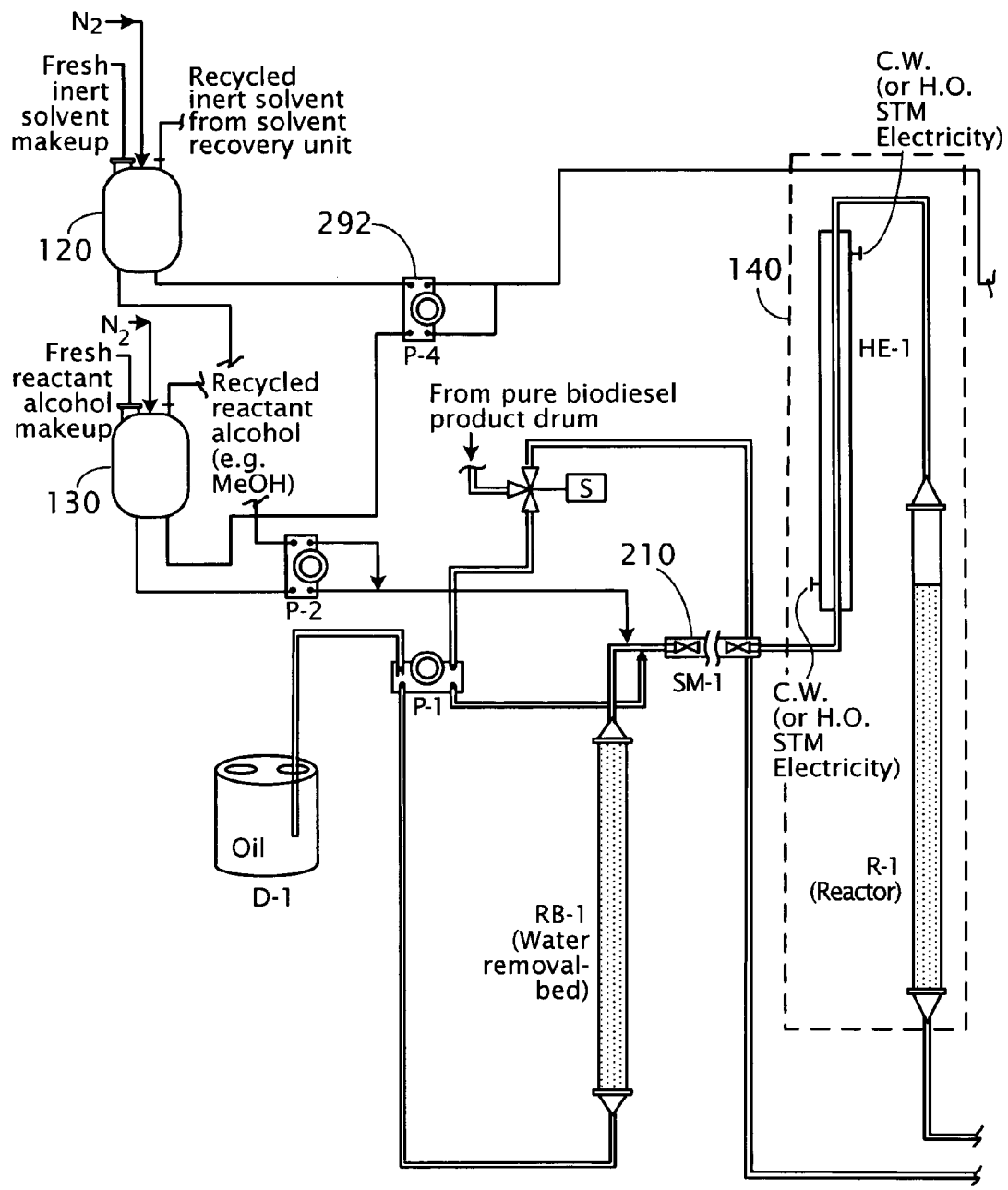
FIGS. 6A-C are enlarged views of portions of FIG. 6.
Figure 6B:
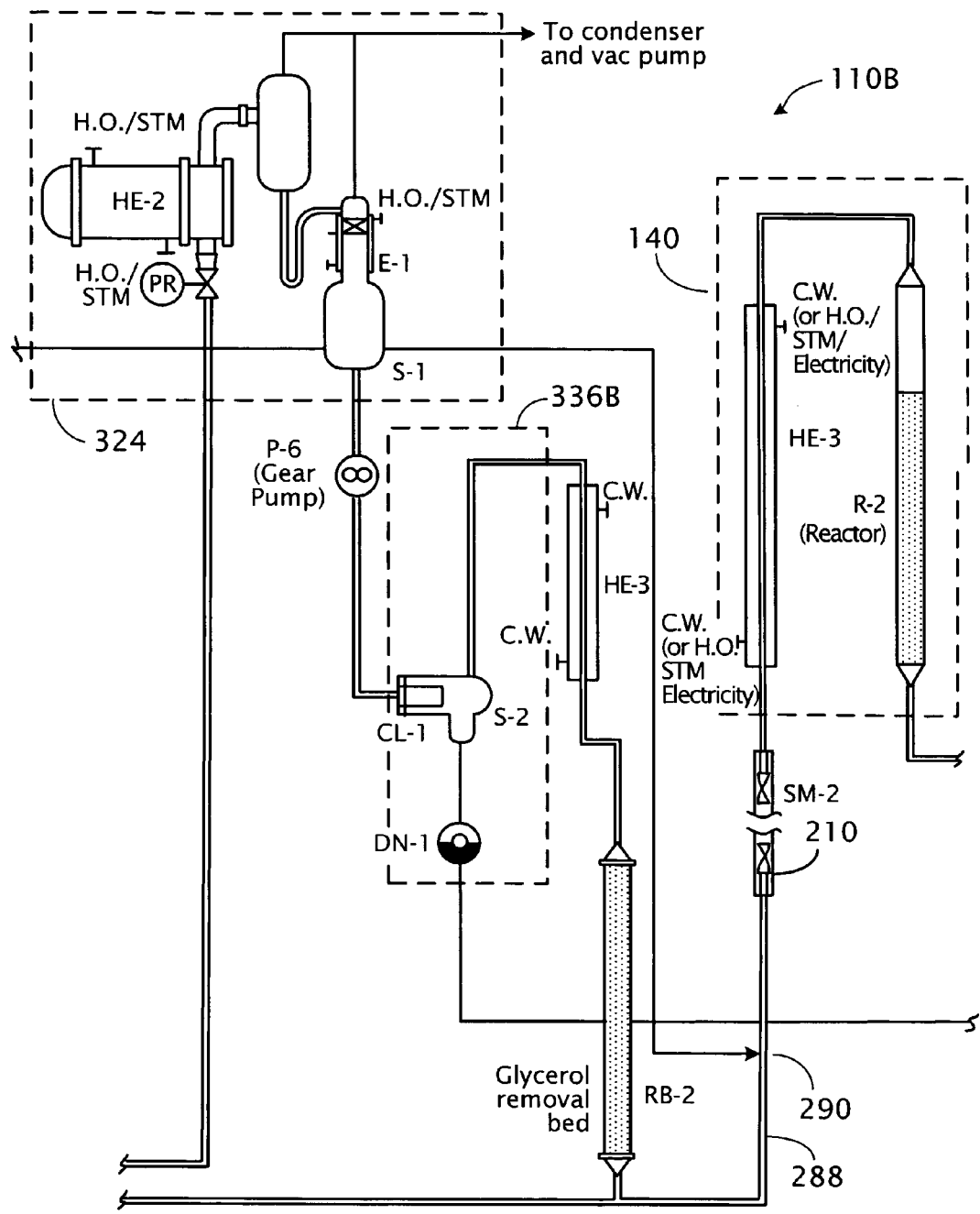
Figure 6C:
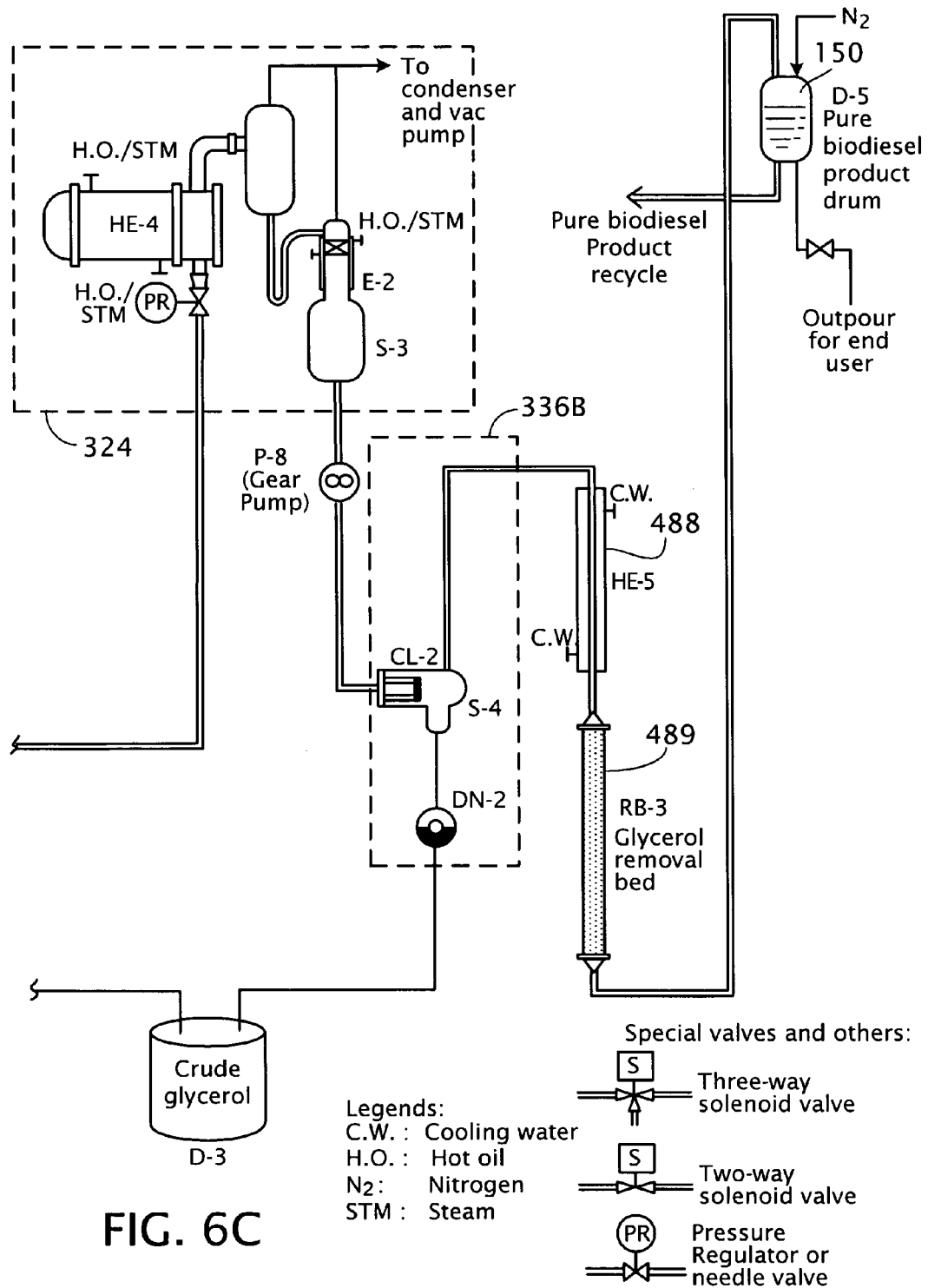

Referring to FIG. 6, an example of a two-stage processing plant 110B of the configuration shown in FIG. 2B is described in detail below. The final separator 230 in FIG. 2B is omitted in FIG. 6.

The first portion of the processing plant 100B in FIG. 6 includes a first reactor 140, a first evaporator 324, and a first coalescer and separator 336B, which operates similarly to corresponding elements in FIG. 5. Instead of using a short path evaporator 344 as in FIG. 5, the processing plant 110B of FIG. 6 uses a second reactor 140, a second evaporator 324, and a second coalescer and separator 336B. The second reactor 140, which can be similar to the first reactor 140, includes an enzymatic catalyst, such as a lipase. The first and second reactors 140 can use the same or different enzymatic catalysts.

The crude biodiesel leaving glycerol removal bed RB-2, which removes glycerol from the crude biodiesel, travels along a pipe 288 towards a second static mixer (SM-2) 210, which is similar to the first static mixer 210 for the first reactor 140. At the same time, a twin-headed pump (P-4) 292 pumps reactant alcohol 130 and inert solvent 120 toward the second static mixer (SM-2) 210 at a rate so that a preset ratio of the reactant alcohol 130 and inert solvent 120 mixes with the crude biodiesel at location 290 before entering the static mixer SM-2 210. The output of the static mixer SM-2 210 is sent to the second reactor 140.

In the second reactor 140, the reactant alcohol, the unreacted oil, and the uncompleted oil react to generate more alkyl ester, so that in an output of the second reactor 140, less unreacted oil and uncompleted oil remains.

The output of the second coalescer and separator 336B includes higher purity biodiesel, which includes a higher percentage (for example, more than 99% by weight) of alkyl ester. The higher purity biodiesel, which may include a trace amount of glycerol, is cooled first in the cooler (HE-5) 488 and then passed through the resin bed (RB-3) 489. The resin bed (RB-3) is filled with a resin to remove trace amount of glycerol.

The final product—high purity biodiesel 150, which may include, for example, 99% by weight of alkyl ester, is sent to a high purity product drum (D-5). The high purity biodiesel in the drum D-5 can be recycled during the start-up or provided to a user.

In some examples, the operating conditions for processing plants 100A (FIGS. 4 and 5) and 100B (FIG. 6) can be as follows. The first reactor 404 operates at temperatures ranging from 0° C. to 95° C., in which the residence time ranges from 1 to 180 minutes. The first evaporator 451 operates at temperatures less than 120° C. and pressures less than 100 mmHg. The removal beds 436, 444, and 461 can be operated at temperatures ranging from 20° C. to 80° C., preferably near room temperature (for example, 25° C.). Coalescers 454 and 456 can be operated at temperatures ranging from 20° C. to 80° C.

6 Exemplary Operating Conditions 6.1 EXAMPLE 1

The following is an example of operation conditions for a two-stage processing plant described above, in which crude biodiesel was recycled to the first reactor inlet. Thin-film evaporators were used, and a short-path evaporator was not used. Refined soybean oil purchased from a local supermarket was used as the feedstock to the processing plant. The amount of water in the refined soybean oil was about 200~300 ppm. Pure anhydrous methanol was used as the reactant alcohol. Pure anhydrous t-amyl alcohol was used as the inert solvent. The first reactor (R-1) included a packed bed filled with lipase, in which the lipase was TL IM, from Novozymes. The residence time of the solution in the first reactor was 50 minutes, and the reaction temperature was 25° C. The second reactor (R-2) was a packed bed filled with lipase, in which the lipase was Novo 435, from Novozymes. The residence time of the solution in the second reactor was 115 minutes, and the reaction temperature was 25° C. The evaporators are wiped thin film evaporators, operating at a temperature of 110° C. and a pressure of 1.0 mmHg abs., and at a rotation speed of 250 revolutions per minute. The final product included 99.10 wt % biodiesel, 0.62 wt % monoglyceride, 0.22 wt % diglyceride, 0.066 wt % triglyceride, and the acid number was 0.630 mg KOH/g.

6.2 EXAMPLE 2

The following is an example of operation conditions for a single-stage processing plant described above, in which crude biodiesel was recycled to the reactor inlet. Two alternative evaporator designs were used: (1) a simple flash drum integrated with a packed bed evaporator, and (2) a thin-film evaporator. The final product was treated by a short-path evaporator. The feedstock was refined fresh soybean oil with water moisture 200-300 ppm. The reactor (R-1) was a packed bed filled with lipase. The lipase was TL IM (from Novozymes), the residence time was 53 minutes, and the reaction temperature was 25° C. When the evaporator (E-1) used a simple flash drum integrated with a packed bed, the operation temperature was 120° C., and the pressure was 5 torr abs. When the evaporator used a thin-film evaporator without flash drum in precedence, the operation temperature was 120° C., the pressure was 1 torr abs, and the rotation rate was 250 revolutions per minute. The final separator used a short-path evaporator (E-2), in which the operation temperature was 120° C., the pressure was 0.05 torr abs, and the rotation rate was 400 RPM. The end product that was obtained included 99.81 wt % biodiesel, 0.13 wt % monoglyceride, 0.06 wt % diglyceride, and non-detectable amount of triglyceride, and the acid number is 0.770 mg KOH/g.

6.3 EXAMPLE 3

The following is an example of operation conditions for a single-stage processing plant described above, in which the crude biodiesel was not recycled. The feedstock was refined fresh soybean oil with water moisture 200-300 ppm. The reactor (R-1) was a packed bed filled with lipase. The lipase was TL IM (from Novozymes), the residence time was 66.6 minutes, and the reaction temperature was 25° C. The evaporator (E-1) was a simple flash drum integrated with a packed bed, operating at temperature 120° C. and pressure 5 torr abs. The end product that was obtained included 86.55 wt % biodiesel, 6.52 wt % monoglyceride, 5.24% diglyceride, and 1.69 wt % triglyceride.

6.4 EXAMPLE 4

The crude biodiesel product that is output from a typical membrane type coalescer (pore size in the range of 1-5 μm) may have an amount of 1,000-1,500 ppm glycerol after the liquid-liquid separation. The crude biodiesel can be passed through a resin bed having a depth of 90 cm, in which the residence time of the fluid in the bed is about 25 minutes. The final glycerol concentration in the effluent can be less than 15 ppm. The resin that is used can be a type of ion exchange resin, MonoPlus SP112, available from Bayer Company, Germany. The saturated bed can be regenerated by methanol, ethanol or equivalent materials.

7 Catalyst Cartridges

The first and second reactors 140 can use removable cartridges filled with enzymatic catalysts, so that old cartridges can be replaced by new ones when the catalysts become ineffective after long run. The first and second reactor 140 are configured to accept a variety of removable cartridges, such as from different vendors, or having different types of catalysts. The processing plants 100A to 100D can be designed to have a coupling mechanism that mate with the cartridges, so that the cartridges can be easily removed and installed. Different types of enzymatic catalysts can be used, each catalyst associated with a different set of operating conditions, such as flow speed and operation temperature. The biodiesel fuel production systems may adjust operation conditions based on the particular type of enzymatic catalyst being used.

Figure 7:
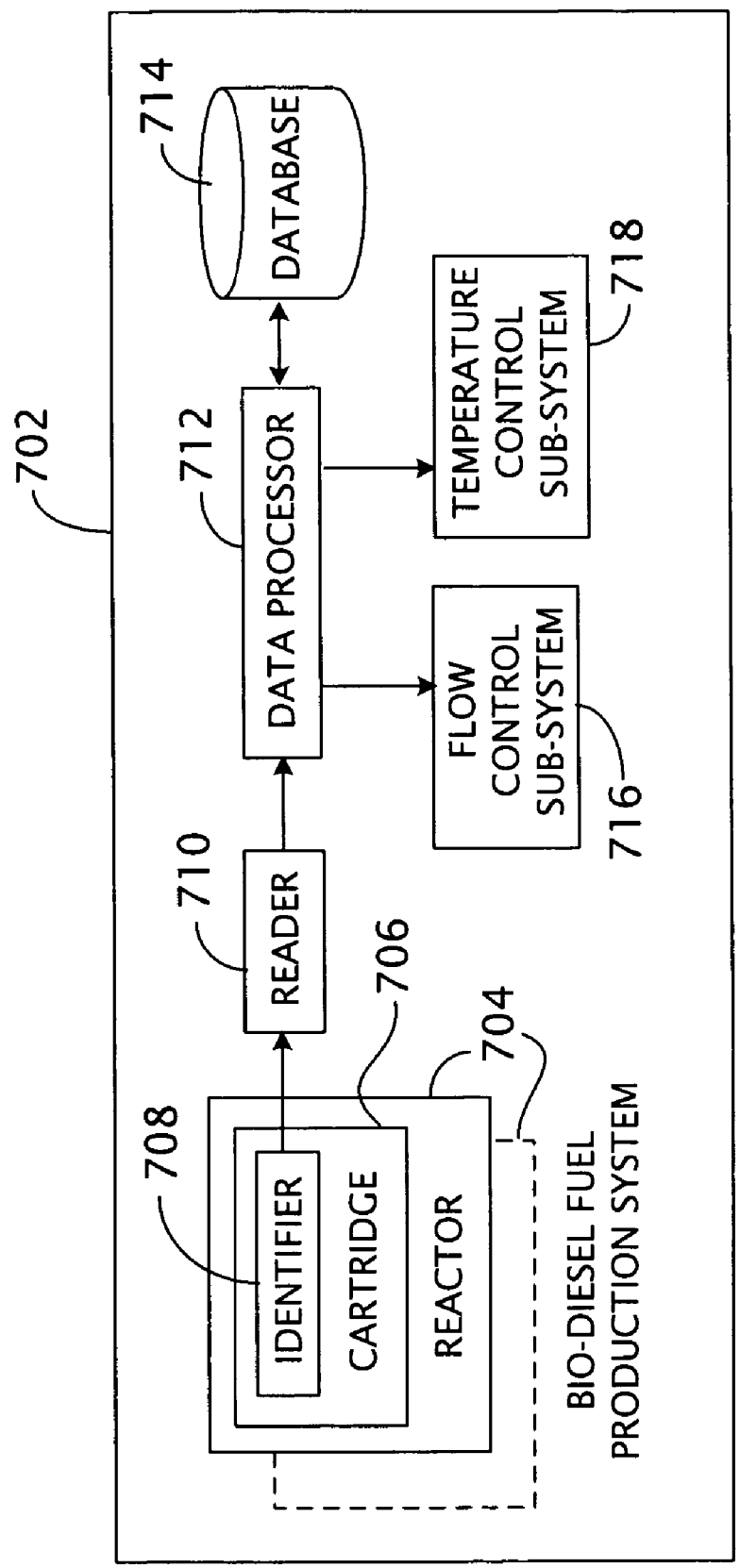
FIG. 7 is a block diagram of fuel production system.

Referring to FIG. 7, a biodiesel fuel production system 702 includes reactors 704, each including a cartridge 706 filled with enzymatic catalyst. The cartridge 706 includes an identifier 708, such as a bar code or a radio frequency identification (RFID) tag, that identifies the enzymatic catalyst in the cartridge 706. A reader 710 (for example, a bar code or RFID reader) reads the identifier 708, and forwards identification information to a data processor 712. Based on the identification information, the data processor 712 retrieves pre-stored operation information from a database 714, and uses the operation information to control a flow control sub-system 716 and a temperature control sub-system 718.

The flow control sub-system 716 includes, for example, pumps that determine a flow speed of the oil source and the reactant alcohol flowing through the reactors. In some examples, the identifier 708 may be associated with an enzymatic catalyst that requires a short residence time, so the data processor 712 controls the flow control sub-system 716 to pump the solutions through the reactors 704 faster. In some examples, the identifier 708 may be associated with an enzymatic catalyst that requires a longer residence time, so the data processor 712 controls the flow control sub-system to pump the solutions through the reactors 704 slower. In some examples, the identifier 708 may be associated with an enzymatic catalyst that requires a higher reaction temperature, so the data processor 712 controls the temperature control sub-system 718 to set the temperatures of the reactors or the heat exchangers at a higher value. In some examples, the identifier 708 may be associated with an enzymatic catalyst that requires a lower reaction temperature, so the data processor 712 controls the temperature control sub-system 718 to set the temperatures of the reactors or the heat exchangers at a lower value.

In some examples, the identifier 708 may be associated with pre-stored information that provides an estimate about when the cartridge 706 needs to be replaced. The pre-stored information may indicate that the cartridge 706 needs to be replaced after a certain volume of solution has passed the cartridge 706. Based on flow meters (not shown) in the system, the data processor 712 determines the volume of solution that has passed the cartridge 706. When the volume exceeds a certain limit, the data processor 712 displays a message to the user to indicating that the cartridge needs to be replaced.

8 Applications

Figure 8:
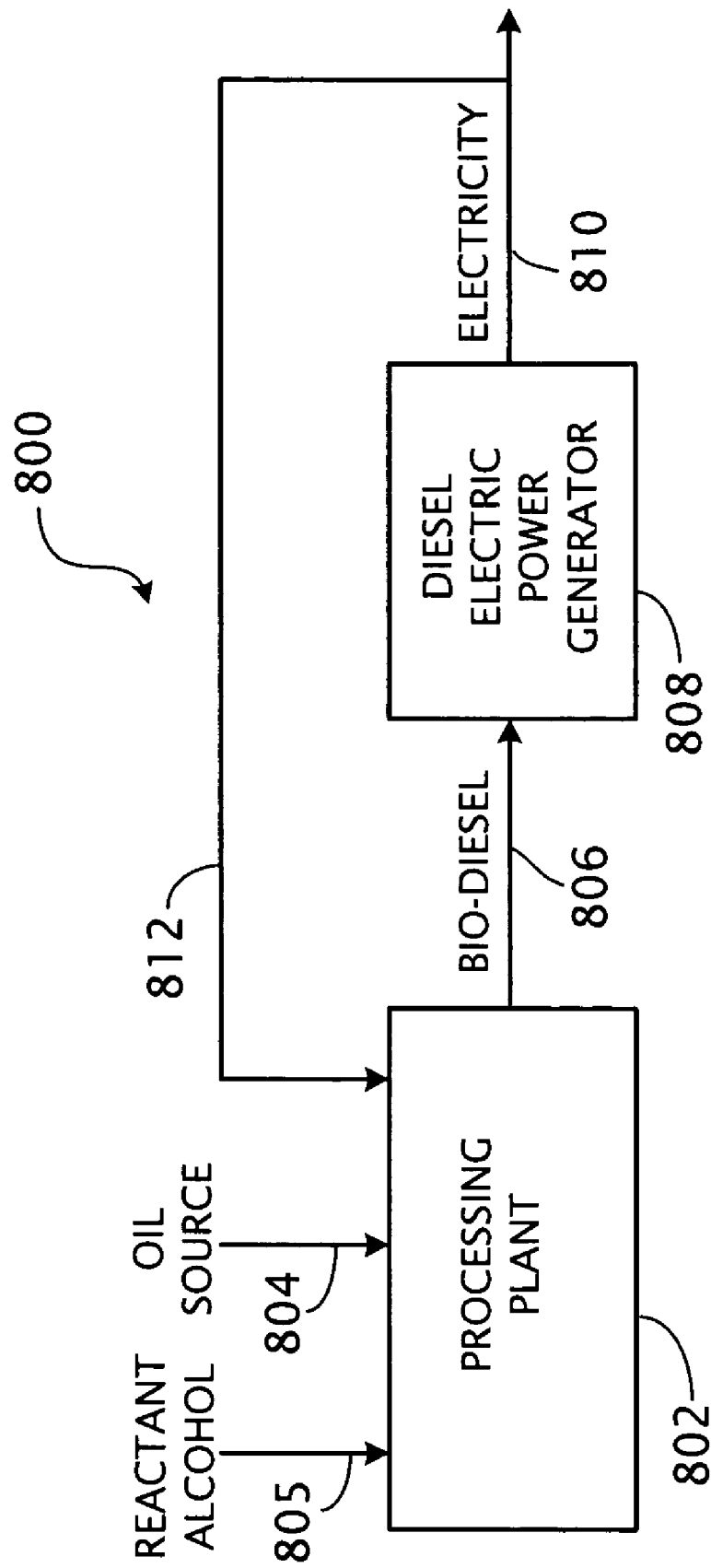
FIG. 8 is a block diagram of a fuel production system coupled to an electric generator.

Referring to FIG. 8, an electric power generator 800 includes a processing plant 802 that receives oil source 804 and reactant alcohol 805, and generates biodiesel 806. The biodiesel 806 is sent to a biodiesel electric power generator 808, which generates electricity 810 from the biodiesel 806. A portion of the electricity is sent to the processing plant 802 through a path 812, and used to provide power to various electrical components of the processing plant.

The system 802 can be any of the processing plants described above.

An advantage of the electric power generator 800 is that the system can generate electricity with less pollution than electric power generators that use petroleum-based diesel fuel. If the oil source includes triglyceride, the generator 800 produces glycerol, water, and carbon dioxide as by-product. If the oil source includes carboxylic acid, the generator 800 products only water and carbon dioxide as by-product.

Figure 9:
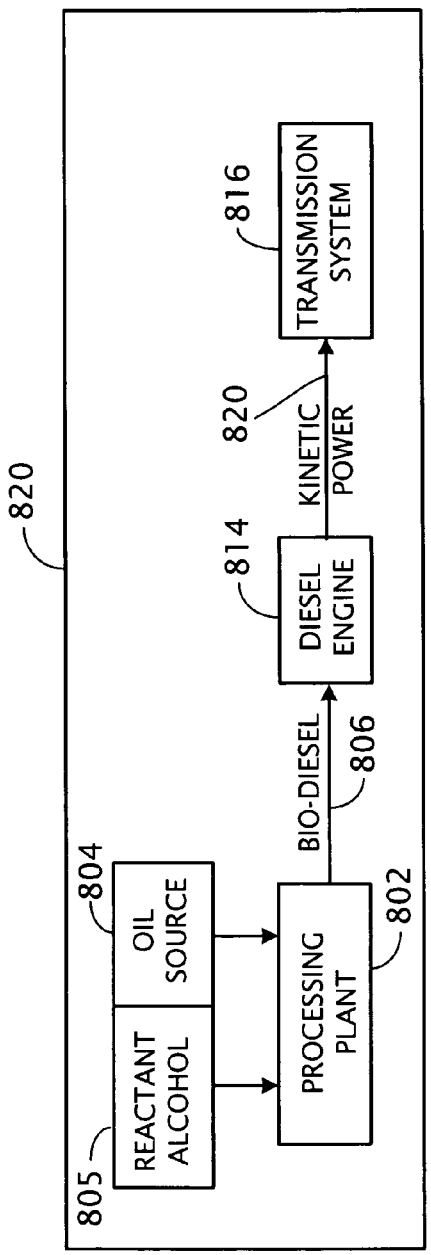
FIG. 9 is a block diagram of a vehicle having a fuel production system.

Referring to FIG. 9, a vehicle 820 includes a processing plant 802 that receives oil source 804 and reactant alcohol 805, and generates biodiesel 806. The biodiesel 806 is sent to a diesel engine 814, which converts the biodiesel into kinetic power 820 that is sent to a transmission system 816 that transmits the kinetic energy to wheels or propellers for powering the vehicle 820. The vehicle 820 may include an electric power generator (not shown) that converts the kinetic energy from the diesel engine into electricity. The electricity can be used to power various electrical components of the vehicle 820.

The processing plant 802 can be any of the processing plants described above. The vehicle 820 can be, for example, a car, a truck, a train, a ship, or an airplane.

Figure 10:
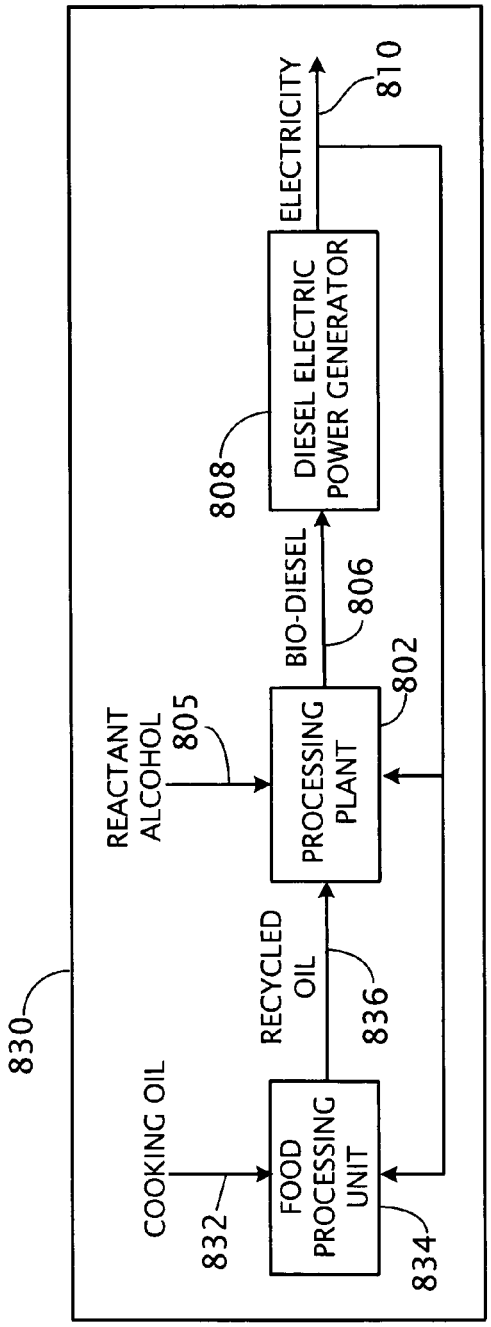
FIG. 10 a block diagram of a fuel production system coupled to a fuel processing unit.

Referring to FIG. 10, a building 830, such as a restaurant, includes a food processing unit 834 (such as a kitchen) that receives cooking oil 832 for processing food. Recycled oil 836 generated by the food processing unit 834 is forwarded to a processing plant 802, which also receives reactant alcohol 805 and outputs biodiesel 806. A diesel electric power generator 808 receives the biodiesel and generates electricity, which is used to power various electrical components of the food processing unit 834 and the processing plant 802.

9 Alternatives

It is to be understood that the foregoing description is intended to illustrate and not to limit the scope of the invention, which is defined by the scope of the appended claims. Other embodiments are within the scope of the following claims. For example, the twin headed pumps can be replaced by two independent pumps. The static mixers can be replaced by an agitated mixing drum or dosing-type static mixers. For small scale production of biodiesel, a dosing type compact static mixer can be used at each mixing point. If the oil source includes a high percentage of water, such as more than 2,000 ppm, the water removal bed can be replaced with a hot air stripping apparatus. The water can be removed by stripping, and the oil is cooled before being sent to the reactor. In some examples, when animal fats or high melting point plant oils are used as the feedstock, the fats or oils are dissolved in the inert solvent first.

If the oil source includes carboxylic acid, a reaction between the carboxylic acid and the reactant alcohol generates alkyl ester, with water as by-product. Glycerol is not generated in this circumstance. Because there is no glycerol, purification of the alkyl ester can be achieved by evaporating the solvent, the unreacted alcohol, and water. When the oil source includes carboxylic acid, it is not necessary to use the separators for separating biodiesel from the glycerol, or to use removal beds for removing glycerol.

In some examples, the biodiesel can be used as fuel for an internal combustion diesel engine or a gas turbine diesel engine.

In some examples, cartridges filled with enzymatic catalysts are used in the reactors of small unit processing plants. For larger commercial units, an on-line loading and downloading of the lipase can embedded in the system design.

In some examples, the evaporator E-1 (FIGS. 4-6) can be a simple flash drum with or without integration of a packed bed design. In other examples, when higher alcohol (reactant alcohol or inert solvent) are used, thin-film evaporators can be employed.

In some examples, the coolers (HE-1, HE-3, HE-5, and HE-6) in the same processing plant can be lumped into one unit for small scale systems. In some examples, the coolers are separate, but placed in parallel in a box, and have a common inlet and a common outlet for the cooling medium, such as cooling water. In some examples, the coolers are designed as air coolers using one fan to cool all streams simultaneously.

In some examples, a short-path evaporator can use a flash drum in inlet similar to that of evaporator E-1. This kind of design can reduce the condenser load inside the short-path unit, which means a higher rate of inlet can be obtained. An external condenser for condensing the evaporated vapor leaving the flash drum can be used. The condensate is lumped to the distillate product of the short path unit.

Regeneration of glycerol removal bed can be on line processing (such as when parallel designs are used for large systems) or off-line processing (such as when cartridge type designs are used for small units).

During shut-down, the whole fuel production system can be blanketed by nitrogen to block moisture and air (to reduce acidification of the biodiesel or the oil source).

In some examples, the glycerol removal resin can be an ion exchange resin, such as Lewatit MonoPlus SP112, available from Bayer Chemical, Leverkusen, Germany.

The static mixer can be replaced by an agitated mixer (drum) with its output rate regulated by a level control.

What is claimed is:

1. An apparatus for producing alkyl ester comprising:
a first reactor having
an inlet to receive a mixture comprising a first reactant, a second reactant, a reaction product, and an inert solvent that dissolves at least a portion of the first and second reactants,
an enzyme to facilitate a reaction between the first and second reactants to generate more reaction product, and
an outlet to output the reaction product, including the reaction product received at the inlet and the reaction product generated from the reaction between the first and second reactants;
a separator which is fed with the reaction product from the outlet of the first reactor, and outputs a crude reaction product including alkyl ester and glycerol, the separator including an evaporator and a liquid-liquid phase separator; the liquid-liquid phase separator separating the alkyl ester from the glycerol; and
a return mechanism to send a portion of the alkyl ester output from the separator back to the inlet.

2. The apparatus of claim 1 in which the mixture includes a solvent that dissolves at least a portion of the first reactant, the second reactant, and the reaction product.

3. The apparatus of claim 2 in which the separator outputs at least the alkyl ester, the solvent, and unreacted first reactant.

4. The apparatus of claim 3, wherein the evaporator is configured to evaporate the solvent to generate a mixture comprising the alkyl ester and the unreacted first reactant.

5. The apparatus of claim 3 in which the separator also outputs glycerol.

6. The apparatus of claim 5, wherein the evaporator is configured to evaporate the solvent to generate a mixture comprising the alkyl ester, the glycerol, and the unreacted first reactant.

7. The apparatus of claim 1 in which the first reactant comprises triglyceride.

8. The apparatus of claim 1 in which the first reactant comprises a carboxylic acid.

9. The apparatus of claim 1 in which the second reactant comprises at least one of a primary and secondary alcohol.

10. The apparatus of claim 1 in which the first reactant comprises at least one of vegetable oil and animal fat.

11. The apparatus of claim 10 in which the reaction product has a composition that is suitable for use as fuel.

12. The apparatus of claim 1, further comprising
a second reactor having
an inlet to receive a mixture comprising additional second reactant and another portion of the alkyl ester output from the separator,
an enzyme to facilitate a reaction between the second reactant and the other components to generate more reaction product, and
an outlet to output the reaction product, including the reaction product received at the inlet of the second reactor and the reaction product generated from the reaction between the second reactant and the other components.

13. The apparatus of claim 12, further comprising a second evaporator to evaporate the inert solvent and at least one of unreacted first reactant and unreacted second reactant.

14. The apparatus of claim 13, further comprising a short-path evaporator which is fed with the reaction product output from the second evaporator to separate the reaction product from remaining unreacted reactant.

15. The apparatus of claim 14 in which the reaction product comprises alkyl ester.

16. The apparatus of claim 1, further comprising a short-path evaporator, which is fed with the reaction product output from the separator, to further separate the reaction product from remaining unreacted reactant.

17. The apparatus of claim 1, further comprising:
a mixer to mix an oil source and a primary alcohol or a secondary alcohol in an organic solvent to form a solution, the oil source including a triglyceride, the reactor being configured to receive the solution and further comprising a lipase that facilitates a reaction between the triglyceride and the primary alcohol or secondary alcohol to generate the alkyl ester, in which glycerol is produced as a by product.

18. The apparatus of claim 17, further comprising a carrier, wherein the lipase is immobilized on the carrier.

* * * * *

UNITED STATES PATENT AND TRADEMARK OFFICE
CERTIFICATE OF CORRECTION

PATENT NO.       : 7,666,666 B2                                            Page 1 of 1
APPLICATION NO.  : 11/232467
DATED            : February 23, 2010
INVENTOR(S)      : Chih-Chung Chou It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1135 days.

Signed and Sealed this

Fourth Day of January, 2011

David J. Kappos
*Director of the United States Patent and Trademark Office*